United States Patent
Huh et al.

(10) Patent No.: US 10,676,512 B2
(45) Date of Patent: Jun. 9, 2020

(54) MICROORGANISM WITH ENHANCED L-LYSINE PRODUCIBILITY AND METHOD FOR PRODUCING L-LYSINE USING THE SAME

(71) Applicant: CJ CHEILJEDANG CORPORATION, Seoul (KR)

(72) Inventors: Lan Huh, Anyang-si (KR); Kwang Ho Lee, Daejeon (KR); Hyung Joon Kim, Seoul (KR); Jun Ok Moon, Seoul (KR); Song-Gi Ryu, Seoul (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 0 days.

(21) Appl. No.: 15/508,662

(22) PCT Filed: Sep. 4, 2015

(86) PCT No.: PCT/KR2015/009353
§ 371 (c)(1),
(2) Date: Jul. 21, 2017

(87) PCT Pub. No.: WO2016/036191
PCT Pub. Date: Mar. 10, 2016

(65) Prior Publication Data
US 2018/0037615 A1    Feb. 8, 2018

(30) Foreign Application Priority Data
Sep. 5, 2014  (KR) .................... 10-2014-0119137

(51) Int. Cl.
| | | |
|---|---|---|
| *C12N 9/12* | (2006.01) | |
| *C07K 14/34* | (2006.01) | |
| *C12P 13/08* | (2006.01) | |
| *C12R 1/15* | (2006.01) | |

(52) U.S. Cl.
CPC .............. *C07K 14/34* (2013.01); *C12N 9/12* (2013.01); *C12P 13/08* (2013.01); *C12R 1/15* (2013.01); *C12Y 207/07006* (2013.01)

(58) Field of Classification Search
None
See application file for complete search history.

(56) References Cited

U.S. PATENT DOCUMENTS

| | | | |
|---|---|---|---|
| 7,524,657 B2 * | 4/2009 | Bathe .................... | C07K 14/34 |
| | | | 435/106 |
| 2009/0170154 A1 | 7/2009 | Endo et al. | |
| 2011/0300588 A1 | 12/2011 | Santos et al. | |

FOREIGN PATENT DOCUMENTS

| | | |
|---|---|---|
| WO | 03/054179 A1 | 7/2003 |
| WO | 2013/095071 A2 | 6/2013 |
| WO | 2013/105802 A2 | 7/2013 |

OTHER PUBLICATIONS

Alper et al., "Global Transcription machinery engineering: A new approach for improving cellular phenotype," *Metabolic Engineering* 9:258-267 (2007).
NCBI Reference Sequence: WB_011014748.1 (May 15, 2013).
Oguiza et al., "Multiple Sigma Factor Genes in *Brevibacterium lactofermentum*: Characterization of sigA and sigB," *Journal of Bacteriology* 178(2):550-553 (Jan. 1996).
Patek et al., "Sigma factors and promoters in *Corynebacterium gluatamicum*," *Journal of Biotechnology* 154:101-113 (2011).
Gomez et al., "sigA is an essential gene in *Mycobacterium smegmatis*," *Molecular Microbiology* 29(2):617-628, 1998.
Halgasova et al., "Cloning and Transcriptional Characterization of Two Sigma Factor Genes, sigA and sigB, from *Brevibacterium flavum*," *Current Microbiology* 43:249-254, 2001.

\* cited by examiner

*Primary Examiner* — Richard G Hutson
(74) *Attorney, Agent, or Firm* — Seed IP Law Group LLP

(57) ABSTRACT

The present disclosure relates to a novel modified RNA polymerase sigma factor A (SigA) polypeptide; a polynucleotide encoding the same; a microorganism containing the polypeptide; and a method for producing L-lysine using the microorganism.

7 Claims, No Drawings

Specification includes a Sequence Listing.

MICROORGANISM WITH ENHANCED L-LYSINE PRODUCIBILITY AND METHOD FOR PRODUCING L-LYSINE USING THE SAME

STATEMENT REGARDING SEQUENCE LISTING

The Sequence Listing associated with this application is provided in text format in lieu of a paper copy, and is hereby incorporated by reference into the specification. The name of the text file containing the Sequence Listing is 200187_430USPC_SEQUENCE_LISTING.txt. The text file is 51.1 KB, was created on Feb. 26, 2017, and is being submitted electronically via EFS-Web.

TECHNICAL FIELD

The present disclosure relates to a novel modified RNA polymerase sigma factor A (SigA) polypeptide; a polynucleotide encoding the same; a microorganism containing the polypeptide; and a method for producing L-lysine using the microorganism.

BACKGROUND ART

Microorganism strains with enhanced producibility can be developed via discovery and appropriate utilization of genetic factors, which are directly/indirectly involved in the early stages of glycolysis, for the preparation of strains producing useful products such as amino acids on a large scale. Representative examples of the technologies to be used for this purpose may include global transcription machinery engineering (gTME), which is an approach to regulate the expression of all of the genes in a cell by inducing random mutagenesis to the recruiting proteins of RNA polymerase. For instance, a research group in the Massachusetts Institute of Technology has shown success in significantly enhancing tyrosine producibility in *E. coli* using the gTME technology (U.S. Pat. No. 8,735,132).

The RNA polymerase used in the transcription step in microorganisms is a macromolecule consisting of 5 small subunits, i.e., two $\alpha$ factors, one $\beta$ factor, one $\beta'$ factor, and one co factor, and its holoenzyme is indicated by $\alpha_2\beta\beta'\omega$. Sigma ($\sigma$) factors, together with the holoenzyme, are essential factors for the initiation step of transcription, which provides a promoter-binding specificity of RNA polymerase. A *Corynebacterium* strain has 7 kinds of sigma factors (SigA, SigB, SigC, SigD, SigE, SigH, and SigM) which regulate the transcription of particular gene groups according to the changes in external environment (*Journal of Biotechnology* 154. 2011. 101-113). In particular, SigA is a major regulator among the sigma factors involved in the regulation of most housekeeping genes and core genes. According to the previous study reports, attempts were made to improve the producibility of target materials by random mutagenesis of SigA (*Metabolic Engineering* 9. 2007. 258-267) and there was also a report regarding the study of increasing L-lysine producibility using a *Corynebacterium* strain (International Publication No. WO 2003-054179).

DISCLOSURE

Technical Problem

Under the circumstances, the present inventors have made efforts to develop a microorganism having L-lysine producibility in an increased concentration without inhibiting the growth of a host cell. As a result, they have confirmed that a microorganism of the genus *Corynebacterium* with enhanced L-lysine producibility can be developed by introducing a novel modified type of SigA polypeptide of RNA polymerase into the microorganism after the development of the microorganism, thereby completing the present disclosure.

Technical Solution

An object of the present disclosure is to provide a modified polypeptide consisting of an amino acid sequence of SEQ ID NO: 2 having an RNA polymerase sigma factor A activity, in which a part of the amino acids of the polypeptide is substituted.

Another object of the present disclosure is to provide a polynucleotide encoding the modified polypeptide.

A further object of the present disclosure is to provide a transformed microorganism encoding the polypeptide.

A still further object of the present disclosure is to provide a method for producing L-lysine, including obtaining a cultured medium by culturing the microorganism and recovering L-lysine from the cultured medium or the cultured microorganism.

Advantageous Effects of the Disclosure

The present disclosure enables confirmation of whether any modified polypeptide having a modified RNA polymerase sigma factor A can upregulate L-lysine producibility. Additionally, based on the above, the microorganism capable of expressing the corresponding modified polypeptide has extremely excellent L-lysine producibility. Accordingly, the microorganism is expected to provide the effects of production cost reduction, convenience in production, etc., from the industrial aspect.

BEST MODE

To achieve the above objects, in an aspect, the present disclosure provides a modified polypeptide having a novel RNA polymerase sigma factor A activity.

As used herein, the term "RNA polymerase sigma factor A (SigA)" refers to a transcription initiation factor which acts along with RNA polymerase, and it is a protein (SigA) corresponding to one of the sigma factors. Sigma factors are involved in the regulation of transcription by interacting with upstream DNA (an UP element), which is present upstream of a particular promoter, and various transcription factors. In particular, SigA is known as a major regulator controlling most of the core genes. Information on the SigA protein can be obtained from a known database such as NCBI GenBank, e.g., a protein having the Accession No. of NP_601117. Specifically, the SigA protein may include the amino acid sequence of SEQ ID NO: 2, but the sequence is not limited thereto as long as the protein has the same activity as that of the SigA of the present disclosure.

As used herein, the term "a modified polypeptide" refers to a polypeptide in which a part or the entirety of the amino acid sequence of a wild-type polypeptide is substituted. In the present disclosure, the modified polypeptide refers to a polypeptide having the RNA polymerase sigma factor A (SigA) activity, in which a part of the amino acid sequence of the polypeptide having the RNA polymerase sigma factor A (SigA) is substituted, thus having an amino acid sequence different from that of the wild-type amino acid sequence.

That is, the present disclosure suggests a SigA-modified polypeptide, which contributes to L-lysine producibility, instead of wild-type SigA polypeptide.

Specifically, the modified polypeptide may be a polypeptide having an RNA polymerase sigma factor A activity, in which at least one amino acid selected from the group consisting of the amino acids at the following positions of a polypeptide consisting of the amino acid sequence of SEQ ID NO: 2 is substituted with another amino acid:

the $136^{th}$ amino acid; the $254^{th}$ amino acid; the $268^{th}$ amino acid; the $281^{st}$ amino acid; the $381^{st}$ amino acid; the $429^{th}$ amino acid; and the $445^{th}$ to $495^{th}$ amino acids, relative to the initiating methionine designated as the first amino acid.

That is, the modified polypeptide may be a polypeptide in which at least one position among the 57 amino acid positions for modification (the $136^{th}$, the $254^{th}$, the $268^{th}$, the $281^{st}$, the $381^{st}$, the $429^{th}$, and the $445^{th}$ to $495^{th}$) is substituted with another amino acid.

More specifically, among the $445^{th}$ to $495^{th}$ amino acids, at least one amino acid selected from the group consisting of the $447^{th}$ amino acid, the $451^{st}$ amino acid, the $455^{th}$ amino acid, the $479^{th}$ amino acid, the $483^{rd}$ amino acid, the $488^{th}$ amino acid, and the $491^{st}$ amino acid may be substituted with another amino acid, but is not limited thereto.

Specifically, the amino acid substitution may be a combination of at least one of the following amino acid substitutions:

a substitution of the $136^{th}$ amino acid with glycine (D136G); a substitution of the $254^{th}$ amino acid with asparagine (I254N); a substitution of the $268^{th}$ amino acid with serine (A268S); a substitution of the $281^{st}$ amino acid with serine (T281S); a substitution of the $381^{st}$ amino acid with arginine (L381R); a substitution of the $429^{th}$ amino acid with arginine (Q429R); a substitution of the $447^{th}$ amino acid with histidine (L447H); a substitution of the $451^{st}$ amino acid with isoleucine (L451I); a substitution of the $455^{th}$ amino acid with valine (M455V); a substitution of the $479^{th}$ amino acid with arginine (K479R); a substitution of the $483^{th}$ amino acid with arginine (K483R); a substitution of the $488^{th}$ amino acid with threonine (S488T); and a substitution of the $491^{st}$ amino acid with arginine (Q491R), relative to the initiating methionine.

More specifically, the polypeptide may be a modified polypeptide, in which the $136^{th}$ amino acid and the $281^{st}$ amino acid are substituted with glycine and serine, respectively (D136G, T281S); the $254^{th}$ amino acid with asparagine (I254N); the $268^{th}$ amino acid with serine (A268S); the $381^{st}$ amino acid with arginine (L381R); the $429^{th}$ amino acid with arginine (Q429R); the $447^{th}$ amino acid with histidine (L447H); the $451^{st}$ and $491^{st}$ amino acids with isoleucine and arginine, respectively (L451I, Q491R); the $455^{th}$ amino acid with valine (M455V); the $479^{th}$ amino acid with arginine (K479R); the $483^{rd}$ amino acid with arginine (K483R); and the $488^{th}$ amino acid with threonine (S488T); relative to the initiating methionine of a polypeptide consisting of the amino acid sequence of SEQ ID NO: 2, or at least one kind among the 11 amino acid substitutions above is combined.

According to an exemplary embodiment of the present disclosure, the modified polypeptide may be a polypeptide having at least one amino acid sequence among the amino acid sequences of SEQ ID NOS: 12 to 22.

The modified polypeptide of the present disclosure includes without limitation not only the amino acid sequences represented by SEQ ID NOS: 12 to 22 but also the amino acid sequences having a homology of 70% or higher, specifically 80% or higher, more specifically 90% or higher, and even more specifically 99%, to the above amino acid sequences, in which the proteins have contributed to the improvement of L-lysine producibility compared to that of the wild-type SigA protein. It is obvious that any amino acid sequence having a biological activity substantially the same as or corresponding to the protein having the amino acid sequence of the modified SigA protein, in addition to the above sequence homology, should also belong to the scope of the present disclosure, although the amino acid may have deletion, modification, substitution, or addition in part of the sequence.

As used herein, the term "homology" refers to a degree of identity between two different sequences of nucleotides or amino acid residues in a particular comparison region of the nucleotide or amino acid sequences of a gene encoding a protein, after aligning both sequences to a maximal match. When the homology is sufficiently high, the expression products of the corresponding gene may have the same or similar activity. The homology may be determined using a sequence comparison program known in the art, e.g., BLAST (NCBI), CLC Main Workbench (CLC bio), MegA-lign™ (DNASTAR Inc.), etc.

Another aspect of the present disclosure includes a polynucleotide encoding the modified polypeptide or a vector including the polynucleotide.

As used herein, the term "polynucleotide" refers to a polymer of nucleotides chain-extended lengthwise by a covalent bond of nucleotide units, i.e., a DNA or RNA strand having at least a certain length, and more specifically, it refers to a polynucleotide fragment encoding the modified polypeptide.

In the present disclosure, the gene encoding the amino acid sequence of the RNA polymerase sigma factor A (SigA) is rpoD gene, and specifically, a gene derived from *Corynebacterium glutamicum*. Based on codon degeneracy, nucleotide sequences encoding the same amino acid and variants thereof belong to the scope of the present disclosure, and specifically, they may be represented by SEQ ID NO: 1, but are not limited thereto.

Additionally, with respect to the modified polypeptide, nucleotide sequences encoding the same amino acid and variants thereof belong to the scope of the present disclosure based on codon degeneracy. Specifically, any nucleotide sequence encoding any of the amino acid sequences 12 to 22 and variants thereof may be included, but are not limited thereto.

Still another aspect of the present disclosure provides a host cell including a polynucleotide encoding the modified polypeptide, and a microorganism transformed with a vector including the polynucleotide encoding the modified polypeptide. Specifically, the introduction may be achieved by transformation, but is not limited thereto.

Specifically, the microorganism including the SigA-modified polypeptide can improve the ability to produce L-lysine without inhibiting the growth of a host cell and thus can obtain L-lysine in high yield compared to the microorganism including the wild-type SigA polypeptide.

As used herein, the term "vector" refers to any carrier for cloning and/or transferring nucleotides into a host cell. A vector may be a replicon to allow for the replication of a fragment combined with another DNA fragment. The term "replicon" refers to any genetic unit acting as a self-replicating unit for in vivo DNA replication, i.e., random genetic units replicable by self-regulation (e.g., plasmids, phages, cosmids, chromosomes, and viruses). As used herein, the term "vector" may include viral and non-viral carriers for introducing nucleotides into a host cell in vitro, ex vivo, or in vivo, and it may also include a mini-spherical DNA. For example, the vector may be a plasmid without a bacterial DNA sequence. Additionally, the vector may include transposons (*Annu Rev Genet*. 2003; 37: 3-29) or artificial chromosomes. Specifically, the vector may include pACYC177, pACYC184, pCL1920, pECCG117, pUC19, pBR322, pDZ, and pMW118 vectors, but is not limited thereto.

As used herein, the term "transformation" refers to a process of introducing a gene into a host cell, thereby enabling the expression of the gene in the host cell. The transformed gene can include without limitation both a gene inserted into the chromosome of a host cell and a gene located outside the chromosome, as long as they can be expressed in the host cell.

Additionally, the gene may be introduced into a host cell in the form of an expression cassette, which is a polynucleotide construct including all essential elements required for self-expression. The expression cassette may conventionally include a promoter operably connected to the gene, a transcription termination signal, a ribosome-binding domain, and a translation termination signal. The expression cassette may be in the form of an expression vector capable of self-replication. Additionally, the polynucleotide may be introduced into a host cell as it is or in the form of a polynucleotide construct, and may be operably connected to a sequence essential for its expression in the host cell, but is not limited thereto.

The host cell or microorganism may be any host cell or microorganism which includes a polynucleotide encoding a modified polypeptide, or which is transformed with a vector including a polynucleotide encoding a modified polypeptide, thus being able to express the modified polypeptide, and for the purpose of the present disclosure, the host cell or microorganism may be any host cell or microorganism that can produce L-lysine by including the SigA-modified polypeptide. Specific examples of the microorganism may include microbial strains belonging to the genus *Escherichia*, the genus *Serratia*, the genus *Erwinia*, the genus *Enterobacteria*, the genus *Salmonella*, the genus *Streptomyces*, the genus *Pseudomonas*, the genus *Brevibacterium*, the genus *Corynebacterium*, etc., and specifically, a microorganism belonging to the genus *Corynebacterium*, and more specifically, *Corynebacterium glutamicum*, but is not limited thereto.

In an exemplary embodiment of the present disclosure, various strains of *Corynebacterium glutamicum* having L-lysine producibility (KCCM11016P, KFCC10750, KCCM10770P, and CJ3P) were introduced with a modified polypeptide which includes any one amino acid sequence selected from the amino acid sequences of SEQ ID NO: 12 to 22, and their L-lysine productivities were compared. As a result, it was confirmed that all strains introduced with the modified polypeptide showed a higher amount of L-lysine production compared to the strain including the wild-type SigA polypeptide (Examples 7 to 10 and Tables 8 to 11). These results suggest that the microorganism including the modified polypeptide of the present disclosure is a strain with enhanced L-lysine producibility and the microorganism provides an economic advantage of obtaining L-lysine in high yield by culturing the microorganism.

As such, the present inventors designated the strain with enhanced L-lysine producibility, "KCCM1016P::SigA (L447H)", as "*Corynebacterium glutamicum* CA01-2277" and deposited it with the Korean Culture Center of Microorganisms, recognized as an international depositary authority under the Budapest Treaty, on Nov. 22, 2013, under the Accession Number KCCM11479P.

Still another aspect of the present disclosure provides a method for producing L-lysine, including culturing the microorganism of the genus *Corynebacterium* described above and recovering L-lysine from the cultured microorganism or the cultured medium.

As used herein, the term "culture" refers to growing a microorganism under appropriately and artificially controlled environmental conditions. The culture process of the present disclosure may be performed based on appropriate culture medium and culture conditions known in the art. Specific conditions, such as culture temperature, culture time, pH of culture medium, etc., may be determined by general knowledge by one of ordinary skill in the art or the conventional method known in the art, and appropriately adjusted accordingly. Specifically, these known culture methods are described in references in detail [Chmiel; Bioprozesstechnik 1. Einfuhrung indie Bioverfahrenstechnik (Gustav Fischer Verlag, Stuttgart, 1991), and Storhas; Bioreaktoren und periphere Einrichtungen (Vieweg Verlag, Braunschweig/Wiesbaden, 1994)]. Additionally, the culture methods may include batch culture, continuous culture, and fed-batch culture, and specifically, the culture may be performed continuously in a fed batch or repeated fed batch process, but is not limited thereto.

The medium used in the culture must appropriately satisfy the requirements for specific strains. Examples of the carbon sources to be used in the medium may include sugars and carbohydrates such as glucose, sucrose, lactose, fructose, maltose, starch, and cellulose; oils and fats such as soybean oil, sunflower oil, castor oil, and coconut oil; fatty acids such as palmitic acid, stearic acid, and linoleic acid; alcohols such as glycerol and ethanol; and organic acids such as acetic acid, but are not limited thereto. These carbon sources may be used alone or in combination, but are not limited thereto. Examples of the nitrogen sources to be used in the medium may include peptone, yeast extract, meat gravy, malt extract, corn steep liquor, soybean flour, and urea or inorganic compounds such as ammonium sulfate, ammonium chloride, ammonium phosphate, ammonium carbonate, and ammonium nitrate. These nitrogen sources may also be used alone or in combination, but are not limited thereto. Examples of the phosphorus sources to be used in the medium may include potassium dihydrogen phosphate, dipotassium hydrogen phosphate, corresponding sodium-containing salts, etc., but are not limited thereto. Additionally, metal salts such as magnesium sulfate or iron sulfate required for growth may be contained in the medium. Lastly, essential materials for growth, such as amino acids and vitamins, may also be contained in addition to the materials described above. Additionally, precursors suitable for a culture medium may be used. These sources may be added to a culture in an appropriate manner during the culture by batch culture or continuous culture, but the methods are not limited thereto.

Additionally, the pH of a culture may be adjusted during the cultivation by adding a compound such as ammonium hydroxide, potassium hydroxide, ammonia, phosphoric acid, and sulfuric acid to the culture in an appropriate manner. During the cultivation, an antifoaming agent, such as fatty acid polyglycol ester, may be added to prevent foam generation. Additionally, oxygen or an oxygen-containing gas may be injected into the culture in order to maintain an aerobic state of the culture; or nitrogen, hydrogen, or carbon dioxide gas may be injected without the injection of a gas in order to maintain an anaerobic or microaerobic state of the culture. The culture temperature may generally be in a range from 27° C. to 37° C., and specifically, from 30° C. to 35° C. The cultivation may be continued until the desired amount of useful materials is obtained, and specifically for from 10 hours to 100 hours. L-lysine may be released into the culture medium being cultured or may be contained in microorganisms.

Additionally, regarding the method of producing L-lysine of the present disclosure, the method of recovering L-lysine from a cultured microorganism or a culture is widely known in the art. The methods of recovering L-lysine may include filtration, anion exchange chromatography, crystallization, HPLC, etc., but are not limited thereto.

DETAILED DESCRIPTION OF THE DISCLOSURE

Hereinafter, the present disclosure will be described in more detail with reference to the following Examples. However, these Examples are for illustrative purposes only, and the disclosure is not intended to be limited by these Examples.

Example 1: Obtaining a SigA-Modified Polypeptide Using an Artificial Mutagenesis In this Example, a vector library for primary crossover-insertion within the chromosome for obtaining a modified SigA was prepared by the following method. Error-prone PCR was performed for rpoD gene (SEQ ID NO: 1) encoding Corynebacterium SigA (SEQ ID NO: 2) and thereby fragments (1497 bp) of rpoD gene variants randomly introduced with a modification of nucleotide substitution were obtained. The error-prone PCR was performed using the GenemorphII Random Mutagenesis Kit (Stratagene), using the genomic DNA of Corynebacterium glutamicum ATCC13032 as a template along with primer 1 (SEQ ID NO: 3) and primer 2 (SEQ ID NO: 4). The error-prone PCR was performed so that modifications can be introduced into the amplified gene fragment at a ratio of 0 to 4.5 mutations per 1 kb of the amplified fragment. PCR was performed for a total of 30 cycles under the following conditions: denaturation at 96° C. for 30 sec, annealing at 53° C. for 30 sec, and polymerization at 72° C. for 2 min.

TABLE 1

| Primer No | Nucleotide Sequence | SEQ ID NO |
|---|---|---|
| 1 | GTGGAGAGCAGCATGGTAG | 3 |
| 2 | CGCAGAGGAAAACAGTGGC | 4 |

The amplified gene fragments were connected to the pCR2.1-TOPO vector (hereinafter, 'pCR2.1') using the pCR2.1-TOPO TA Cloning Kit (Invitrogen), transformed into E. coli DH5a, and plated on solid LB medium. Twenty of the thus-transformed colonies were selected and their nucleotide sequences were analyzed after obtaining their plasmids. As a result, it was confirmed that mutations were introduced at different locations at a frequency of 1.5 mutations/kb. Plasmids were extracted from about 20,000 transformed E. coli colonies and they were named as "pCR2.1-rpoD(mt) library". Then, a plasmid including the wild-type rpoD gene to be used as a control was prepared. PCR was performed using the genomic DNA of Corynebacterium glutamicum ATCC13032 as a template along with primer 1 (SEQ ID NO: 3) and primer 2 (SEQ ID NO: 4), under the same conditions described above. For the polymerase, PfuUltra™ high-fidelity DNA polymerase (Stratagene) was used, and the plasmid prepared as such was named as "pCR2.1-rpoD (WT)".

Example 2: Preparation of a Library of SigA-Modified Strains with Enhanced L-Lysine Producibility The pCR2.1-rpoD(mt) library prepared using the KCCM11016P strain (Korean Pat. No. 10-0159812) as the parent strain was transformed by homologous chromosome recombination, plated on complex medium containing kanamycin (25 mg/L) and the components described below, and about 25,000 colonies were obtained therefrom. The colonies were named as "KCCM11016P/pCR2.1-rpoD(mt)-1" to "KCCM11016P/pCR2.1-rpoD(mt)-25000".

Additionally, the thus-prepared pCR2.1-rpoD(WT) vector was transformed into the KCCM11016P strain to prepare the control strain, and it was named as "KCCM11016P/pCR2.1-rpoD(WT)".

The thus-obtained transformants will have two copies of the rpoD gene on the chromosome. However, pCR2.1-rpoD (mt) library and the pCR2.1-rpoD(WT) vector are inserted with rpoD gene fragments without any promoter, and thus when they are inserted into the chromosome of a strain by homologous recombination, only one copy of the two copies of the rpoD gene is expressed thus capable of expressing a modified- or wild-type SigA protein.

<Complex Medium (pH 7.0)>

Glucose (10 g), Peptone (10 g), Beef Extract (5 g), Yeast Extract (5 g), Brain Heart Infusion (18.5 g), NaCl (2.5 g), Urea (2 g), Sorbitol (91 g), Agar (20 g) (based on 1 L of distilled water)

Example 3: Screening of a Library of SigA-Modified Strains with Improved L-Lysine Producibility About 25,000 colonies obtained in Example 2 were respectively inoculated into selective medium (300 μL) containing the components described below and cultured in a 96-deep well plate at 32° C. at a rate of 1000 rpm for 24 hours. The amount of L-lysine production during the cultivation was analyzed by a ninhydrin method (J. Biol. Chem. 1948. 176: 367-388). Upon completion of the cultivation, 10 μL of the culture supernatant and 190 μL of a ninhydrin reaction solution ((63% glycerol, 27% ninhydrin reaction (7.1 g/L in 0.5 M citrate buffer, pH 5.5)) were reacted at 65° C. for 30 minutes. The absorbance at wavelength 570 nm was measured by a spectrophotometer and was compared to that of the control, i.e., KCCM11016P/pCR2.1-rpoD(WT), and about 935 modified strains showing an absorbance with an at least 10% increase were selected. Other colonies showed similar or reduced absorbance compared to that of the control.

<Selective Medium (pH 8.0)>

Glucose (10 g), Ammonium Sulfate (5.5 g), MgSO$_4$.7H$_2$O (1.2 g), KH$_2$PO$_4$ (0.8 g), K$_2$HPO$_4$ (16.4 g), Biotin (100 μg), Thiamine HCl (1000 μg), Calcium-Pantothenic Acid (2000 μg), and Nicotinamide (2000 μg) (based on 1 L of distilled water)

The above method was repeatedly performed for the selected 935 strains, and the top 231 kinds of strains with an improved L-lysine producibility by 15% or higher compared to that of KCCM1016P/pCR2.1-rpoD(WT) strain.

Example 4: Analysis of L-Lysine Producibility by KCCM11016P/pCR2.1-rpoD(Mt)

The 231 kinds of strains selected in Example 3 were analyzed with respect to their L-lysine productivities after culturing them by the following method.

Each of the strains was inoculated into a 250 mL corner-baffle flask containing 25 mL of seed culture medium, respectively, and cultured in a shaking incubator (200 rpm) at 30° C. for 20 hours. Then, each of the 250 mL corner-baffle flasks containing 24 mL of the culture, which contained the components described below, was inoculated with 1 mL of a seed culture liquid, and cultured in a shaking incubator (200 rpm) at 30° C. for 72 hours. The concentration of L-lysine in each culture was analyzed via high performance liquid chromatography (HPLC).

<Seed Culture Medium (pH 7.0)>

Glucose (20 g), Peptone (10 g), Yeast Extract (5 g), Urea (1.5 g), $KH_2PO_4$ (4 g), $K_2HPO_4$ (8 g), $MgSO_4 \cdot 7H_2O$ (0.5 g), Biotin (100 µg), Thiamine HCl (1000 µg), Calcium-Pantothenic Acid (2000 µg), and Nicotinamide (2000 µg) (based on 1 L of distilled water)

<Production Medium (pH 7.0)>

Glucose (100 g), $(NH_4)_2SO_4$ (40 g), Soybean Protein (2.5 g), Corn Steep Solids (5 g), Urea (3 g), $KH_2PO_4$ (1 g), $MgSO_4 \cdot 7H_2O$ (0.5 g), Biotin (100 µg), Thiamine HCl (1000 µg), Calcium-Pantothenic Acid (2000 µg), Nicotinamide (3000 µg), and $CaCO_3$ (30 g) (based on 1 L of distilled water)

Among the selected 231 kinds of strains, 17 kinds of strains showing a reproducibly increased L-lysine concentration compared to the control were selected, and the cultivation and analysis were performed repeatedly. The analysis results of the L-lysine concentration are shown in Table 2 below.

TABLE 2

| | | L-lysine (g/L) | | | |
|---|---|---|---|---|---|
| | Strain | Batch 1 | Batch 2 | Batch 3 | Mean |
| Control | KCCM11016P/pCR2.1-rpoD(WT) | 41.5 | 42.1 | 41.8 | 41.8 |
| 1 | KCCM11016P/pCR2.1-rpoD(mt)-158 | 45.7 | 45.2 | 48.1 | 46.3 |
| 2 | KCCM11016P/pCR2.1-rpoD(mt)-1494 | 44.8 | 46.2 | 45.7 | 45.6 |
| 3 | KCCM11016P/pCR2.1-rpoD(mt)-1846 | 46.8 | 45.9 | 47.1 | 46.6 |
| 4 | KCCM11016P/pCR2.1-rpoD(mt)-2198 | 49.8 | 47.8 | 47.9 | 48.5 |
| 5 | KCCM11016P/pCR2.1-rpoD(mt)-2513 | 45.2 | 47.3 | 45.6 | 46.0 |
| 6 | KCCM11016P/pCR2.1-rpoD(mt)-3777 | 45.8 | 47.6 | 45.9 | 46.4 |
| 7 | KCCM11016P/pCR2.1-rpoD(mt)-4065 | 50.7 | 49.8 | 49.5 | 50.0 |
| 8 | KCCM11016P/pCR2.1-rpoD(mt)-5329 | 44.5 | 42.5 | 42.8 | 43.3 |
| 9 | KCCM11016P/pCR2.1-rpoD(mt)-6589 | 41.8 | 42.3 | 41.8 | 42.0 |
| 10 | KCCM11016P/pCR2.1-rpoD(mt)-9823 | 47.3 | 46.8 | 47.0 | 47.0 |
| 11 | KCCM11016P/pCR2.1-rpoD(mt)-11267 | 45.5 | 45.3 | 45.1 | 45.3 |
| 12 | KCCM11016P/pCR2.1-rpoD(mt)-13306 | 48.5 | 46.5 | 46.6 | 47.2 |
| 13 | KCCM11016P/pCR2.1-rpoD(mt)-14535 | 48.2 | 49.3 | 47.5 | 48.3 |
| 14 | KCCM11016P/pCR2.1-rpoD(mt)-16323 | 44.2 | 44.6 | 45.8 | 44.9 |
| 15 | KCCM11016P/pCR2.1-rpoD(mt)-17935 | 46.5 | 47.2 | 44.5 | 46.1 |
| 16 | KCCM11016P/pCR2.1-rpoD(mt)-18904 | 42.3 | 41.5 | 42.6 | 42.1 |
| 17 | KCCM11016P/pCR2.1-rpoD(mt)-19803 | 47.2 | 45.3 | 46.3 | 46.3 |

As a result of the analysis of the L-lysine concentration of the 17 selected strains, it was confirmed that the L-lysine producibility of 15 strains excluding the two strains, i.e., KCCM1016P/pCR2.1-rpoD(mt)-6589 and KCCM1016P/pCR2.1-rpoD(mt)-18904, was increased by 20% at maximum compared to that of the control, KCCM11016P/pCR2.1-rpoD(WT) strain.

Example 5: Confirmation of rpoD Gene Mutations in Strains Selected from a Library with Artificial Mutagenesis of SigA To confirm the mutations introduced on SigA in the 15 strains showing an improved L-lysine producibility among the 17 selected strains in Example 4, the nucleotide sequences of rpoD mutants were analyzed. For determining the nucleotide sequences, PCR was performed using primer 1 (SEQ ID NO: 3) and primer 3 (SEQ ID NO: 5).

TABLE 3

| Primer No | Nucleotide Sequence | SEQ ID NO |
|---|---|---|
| 1 | GTGGAGAGCAGCATGGTAG | 3 |
| 3 | AACAGCTATGACCATG | 5 |

The nucleotide sequence of the modified rpoD gene was confirmed based on the NIH Genbank by analyzing the nucleotide sequences of the fragments of the modified rpoD gene for each of the thus-obtained 15 strains, and the nucleotide sequence of the modified SigA was confirmed. The analysis results of the modified SigA amino acid sequence of the thus-obtained 15 strains are shown in Table 4 below.

TABLE 4

| Strain | Modification in Amino Acid(s) of SigA |
|---|---|
| KCCM11016P/pCR2.1-rpoD(mt)-158 | D136G, T281S |
| KCCM11016P/pCR2.1-rpoD(mt)-1494 | L381R |
| KCCM11016P/pCR2.1-rpoD(mt)-1846 | M230T |

TABLE 4-continued

| Strain | Modification in Amino Acid(s) of SigA |
|---|---|
| KCCM11016P/pCR2.1-rpoD(mt)-2198 | M455V |
| KCCM11016P/pCR2.1-rpoD(mt)-2513 | S488T |
| KCCM11016P/pCR2.1-rpoD(mt)-3777 | R279L |
| KCCM11016P/pCR2.1-rpoD(mt)-4065 | L447H |

TABLE 4-continued

| Strain | Modification in Amino Acid(s) of SigA |
|---|---|
| KCCM11016P/pCR2.1-rpoD(mt)-5329 | A268S |
| KCCM11016P/pCR2.1-rpoD(mt)-9823 | L451I, Q491R |
| KCCM11016P/pCR2.1-rpoD(mt)-11267 | Q429R |
| KCCM11016P/pCR2.1-rpoD(mt)-13306 | K90E, K105Y, D250G, I254L |
| KCCM11016P/pCR2.1-rpoD(mt)-14535 | I254N |
| KCCM11016P/pCR2.1-rpoD(mt)-16323 | K483R |
| KCCM11016P/pCR2.1-rpoD(mt)-17935 | K479R |
| KCCM11016P/pCR2.1-rpoD(mt)-19803 | D238V, N263S, E358D |

As a result, it was confirmed that amino acids in a range of a minimum of one to a maximum of four were substituted. In Table 4 above, the figure represents the amino acid number of SigA; the letter in front of the figure represents an amino acid before substitution; and the letter after the figure represents a substituted amino acid.

Example 6: Preparation of a Vector for Introducing an rpoD-Modified Chromosome for the Production of a Strain Having L-Lysine Producibility in High Concentration To confirm the effect of the application of the SigA modification, which was confirmed in Example 4, a vector capable of introducing the SigA modification onto the chromosome was prepared.

The primer 4 (SEQ ID NO: 6), in which an EcoRI restriction site was inserted at the 5' end, and the primer 5 (SEQ ID NO: 7), in which a SalI restriction site was inserted at the 3' end, were synthesized based on the reported nucleotide sequences. Then, PCR was performed using each of the chromosomes of the 15 selected kinds as a template using the primer pair, and thereby 15 kinds of modified rpoD(mt) gene fragments were amplified. PCR was performed under the following conditions: denaturation at 94° C. for 5 min; 30 cycles of denaturation at 94° C. for 30 sec, annealing at 56° C. for 30 sec, and polymerization at 72° C. for 2 min; and polymerization at 72° C. for 7 min.

TABLE 5

| Primer No | Nucleotide Sequence | SEQ ID NO |
|---|---|---|
| 4 | AAGAATTCGTGGAGAGCAGCATGGTAG | 6 |
| 5 | AAGTCGACCGCAGAGGAAAACAGTGGC | 7 |

The 15 kinds of gene fragments amplified by PCR were treated with EcoRI and SalI to obtain the respective DNA fragments, and linked the fragments to the pDZ vector (Korean Pat. No. 10-0924065) for introducing chromosome, which includes EcoRI and SalI restriction sites therein, transformed into E. coli DH5a, and spread on LB solid medium containing kanamycin (25 mg/L). The colonies transformed with a vector inserted with a target gene by PCR were selected and the plasmids were obtained by a conventionally-known plasmid extraction method. The plasmids were named as pDZ-SigA(D136G, T281S), pDZ-SigA(L381R), pDZ-SigA(M230T), pDZ-SigA(M455V), pDZ-SigA(S488T), pDZ-SigA (R279L), pDZ-SigA(I254N), pDZ-SigA(A268S), pDZ-SigA(L451I, Q491R), pDZ-SigA(Q429R), pDZ-SigA(K90E, K105Y, D250G, I254L), pDZ-SigA(L447H), pDZ-SigA(K483R), pDZ-SigA(K479R), and pDZ-SigA(D238V, N263S, E358D), respectively, according to the modification of the insertion on SigA of each plasmid. Additionally, as another control for the above variants, primers 6 to 9 (SEQ ID NOS: 8 to 11) were prepared for the construction of vectors to insert the SigA-modified A414V, which was reported to have an effect of increasing L-lysine producibility (International Publication WO 2003-054179), into the chromosome. Then, PCR was performed using the genomic DNA of Corynebacterium glutamicum ATCC13032 along with a primer pair of primer 6 and primer 9 and a primer pair of primer 7 and primer 8, respectively. PCR was performed under the following conditions: denaturation at 94° C. for 5 min; 30 cycles of denaturation at 94° C. for 30 sec, annealing at 56° C. for 30 sec, and polymerization at 72° C. for 1 min; and polymerization at 72° C. for 7 min.

| Primer No | Nucleotide Sequence | SEQ ID NO |
|---|---|---|
| 6 | GCAGGTCGACTCTAGACTCACCCCAGCCGTCAAGCGT | 8 |
| 7 | CCGGGGATCCTCTAGATCAAGGCGATGTCGGAAAATG | 9 |
| 8 | AAGACTCCGAAGTCGTCGTCGCAGT | 10 |
| 9 | ACTGCGACGACGACTTCGGAGTCTT | 11 |

As a result, gene fragments with a size of about 500 bp were obtained and the amplified products were linked to the pDZ vector using the Infusion cloning kit (Invitrogen). The thus-prepared vector was named as pDZ-SigA(A414V).

Example 7: Preparation of KCCM11016P Strain Introduced with SigA-Modified Polypeptide for Strains Having L-Lysine Producibility in High Concentration and Comparison of their L-Lysine Productivities The 15 kinds of vectors introduced with novel mutations prepared in Example 6 and one kind of a vector introduced with a mutation reported previously were transformed into the Corynebacterium glutamicum KCCM11016P, which is a strain producing L-lysine, by a two-step homologous chromosome recombination. Then, the strains introduced with the SigA modifications were selected by the analysis of nucleotide sequences. The strains introduced with the SigA modifications were named as KCCM11016P::SigA(D136G, T281S), KCCM11016P::SigA(L381R), KCCM11016P::SigA(M230T), KCCM11016P::SigA(M455V), KCCM11016P::SigA(S488T), KCCM011016P::SigA (R279L), KCCM11016P::SigA(I254N), KCCM11016P::SigA(A268S), KCCM11016P::SigA(L451I, Q491R), KCCM11016P::SigA(Q429R), KCCM011016P::SigA (K90E, K105Y, D250G, I254L), KCCM11016P::SigA(L447H), KCCM11016P::SigA(K483R), KCCM011016P::SigA(K479R), KCCM11016P::SigA(D238V, N263S, E358D), and KCCM11016P::SigA(A414V), respectively.

The strains were cultured in the same manner as in Example 4 and their L-lysine concentrations were analyzed. The results are shown in Table 7 below.

TABLE 7

| | Strain | L-lysine (g/L) | | | |
|---|---|---|---|---|---|
| | | Batch 1 | Batch 2 | Batch 3 | Mean |
| Control | KCCM11016P | 42.8 | 41.6 | 43.1 | 42.5 |
| 1 | KCCM11016P::SigA(D136G, T281S) | 46.2 | 45.8 | 45.2 | 45.7 |

TABLE 7-continued

| | | L-lysine (g/L) | | | |
|---|---|---|---|---|---|
| | Strain | Batch 1 | Batch 2 | Batch 3 | Mean |
| 2 | KCCM11016P::SigA(L381R) | 45.2 | 45.8 | 46.7 | 45.9 |
| 3 | KCCM11016P::SigA(M230T) | 41.8 | 42.1 | 41.9 | 41.9 |
| 4 | KCCM11016P::SigA(M455V) | 50.1 | 48.1 | 49.2 | 49.1 |
| 5 | KCCM11016P::SigA(S488T), | 45.1 | 44.9 | 45.8 | 45.3 |
| 6 | KCCM11016P::SigA(R279L) | 42.5 | 43.2 | 40.9 | 42.2 |
| 7 | KCCM11016P::SigA(L447H) | 51.2 | 49.9 | 50.8 | 50.6 |
| 8 | KCCM11016P::SigA(A268S) | 43.2 | 44.1 | 45.5 | 44.3 |
| 9 | KCCM11016P::SigA(L451I, Q491R) | 47.5 | 47.1 | 49.8 | 48.1 |
| 10 | KCCM11016P::SigA(Q429R) | 44.9 | 45.2 | 45.1 | 45.1 |
| 11 | KCCM11016P::SigA(K90E, K105Y, D250G, I254L) | 31.5 | 28.6 | 40.5 | 33.5 |
| 12 | KCCM11016P::SigA (I254N) | 49.1 | 48.5 | 47.8 | 48.5 |
| 13 | KCCM11016P::SigA(K483R) | 45.1 | 44.1 | 45.6 | 44.9 |
| 14 | KCCM11016P::SigA(K479R) | 44.7 | 45.6 | 45.8 | 45.4 |
| 15 | KCCM11016P::SigA(D238V, N263S, E358D) | 21.5 | 22.9 | 19.2 | 21.2 |
| Control | KCCM11016P::SigA(A414V) | 43.2 | 44 | 43.5 | 43.6 |

As a result, two novel strains introduced with modifications (KCCM11016P::SigA(M230T) and KCCM11016P::SigA(R279L)) showed the L-lysine producibility equivalent to that of the parent strain, whereas the other two novel strains introduced with mutations (KCCM11016P::SigA (K90E, K105Y, D250G, I254L) and KCCM11016P::SigA (D238V, N263S, E358D)) showed a significantly low growth rate and a significantly reduced amount of L-lysine production. However, the remaining 11 novel mutant strains showed a maximum increase of 19% in L-lysine production compared to that of the parent strain, and also showed an increase of 16% in L-lysine production compared to that of KCCM11016P::SigA(A414V), which is a mutant strain introduced with SigA(A414V) reported previously. As such, the present inventors designated the strain with an improved L-lysine producibility, "KCCM1016P::SigA(L447H)", as "Corynebacterium glutamicum CA01-2277" and deposited it with the Korean Culture Center of Microorganisms, recognized as an international depositary authority under the Budapest Treaty, on Nov. 22, 2013, under the Accession Number KCCM11479P.

These results suggest that the 11 novel SigA-modified polypeptides have excellent L-lysine producibility.

Example 8: Preparation of KFCC10750 Strain Introduced with SigA-Modified Polypeptide for Strains Having L-Lysine Producibility in High Concentration and Comparison of their L-Lysine Productivities To confirm the effect of the introduction of the 11 kinds of SigA variants, selected in Example 7, in other strains of the genus Corynebacterium glutamicum, the strains respectively introduced with each of the 11 kinds of SigA mutations of Corynebacterium glutamicum KFCC10750 (KCCM11347P, Korean Pat. No. 10-0073610) having L-lysine producibility were prepared in the same manner as in Example 7. These strains were named as KFCC10750::SigA (D136G, T281S), KFCC10750::SigA(L381R), KFCC10750::SigA(M455V), KFCC10750::SigA(S488T), KFCC10750::SigA(I254N), KFCC10750::SigA(A268S), KFCC10750::SigA(L451I, Q491R), KFCC10750::SigA (Q429R), KFCC10750::SigA(L447H), KFCC10750::SigA (K483R), and KFCC10750::SigA(K479R), respectively. Additionally, the strain introduced with the SigA(A414V) mutation, reported previously, was prepared and named as "KFCC10750::SigA(A414V)".

The strains were cultured in the same manner as in Example 4 and their L-lysine concentrations were analyzed. The results are shown in Table 8 below.

TABLE 8

| | | L-lysine (g/L) | | | |
|---|---|---|---|---|---|
| | Strain | Batch 1 | Batch 2 | Batch 3 | Mean |
| Control | KFCC10750 | 38.8 | 38.1 | 37.9 | 38.3 |
| 1 | KFCC10750::SigA(D136G, T281S) | 41.1 | 41.2 | 40.9 | 41.1 |
| 2 | KFCC10750::SigA(L381R) | 42.1 | 41.8 | 41.1 | 41.7 |
| 3 | KFCC10750::SigA(M455V) | 43.2 | 43.8 | 44.2 | 43.7 |
| 4 | KFCC10750::SigA(S488T) | 42.1 | 40.8 | 41.9 | 41.6 |
| 5 | KFCC10750::SigA (L447H) | 44.5 | 45.1 | 44.9 | 44.8 |
| 6 | KFCC10750::SigA(A268S) | 39.9 | 41.1 | 39.7 | 40.2 |
| 7 | KFCC10750::SigA(L451I, Q491R) | 42.9 | 44.1 | 43.8 | 43.6 |
| 8 | KFCC10750::SigA(Q429R) | 40.2 | 41.2 | 42.1 | 41.2 |
| 9 | KFCC10750::SigA(I254N) | 44.9 | 44.5 | 43.8 | 44.4 |
| 10 | KFCC10750::SigA(K483R) | 40.5 | 41 | 40.9 | 40.8 |
| 11 | KFCC10750::SigA(K479R) | 39.9 | 41.5 | 41.1 | 40.8 |
| Control | KFCC10750::SigA(A414V) | 39.6 | 39.1 | 39.5 | 39.4 |

As a result, the 11 kinds of strains introduced with novel mutations showed a maximum increase of 17% in L-lysine production compared to that of the parent strain, and also showed an increase of about 14% in L-lysine production compared to that of KFCC10750::SigA(A414V), which is a strain introduced with the SigAA414V mutation reported previously.

Example 9: Preparation of KCCM10770P Strain Introduced with SigA-Modified Polypeptide for Strains Having L-Lysine Producibility in High Concentration and Comparison of their L-Lysine Productivities To confirm the effect of the introduction of the 11 kinds of SigA variants, selected in Example 7, in other strains of the genus Corynebacterium glutamicum, the strains respectively introduced with SigA modifications of Corynebacterium glutamicum KFCC10770 (KCCM11347P, Korean Pat. No. 10-0924065) having L-lysine producibility were prepared in the same manner as in Example 7. These strains were named as KCCM10770P::SigA(D136G, T281S), KCCM10770P::SigA(L381R), KCCM10770P::SigA (M455V), KCCM10770P::SigA(S488T), KCCM10770P::SigA(I254N), KCCM10770P::SigA(A268S), KCCM10770P::SigA(L451I, Q491R), KCCM10770P::SigA(Q429R), KCCM10770P::SigA(L447H), and KCCM10770P::SigA(K483R), KCCM10770P::SigA (K479R), respectively. Additionally, the strain introduced with the SigA(A414V) mutation, reported previously, was prepared and named as "KFCC10770::SigA(A414V)".

The strains were cultured in the same manner as in Example 4 and their L-lysine concentrations were analyzed. The results are shown in Table 9 below.

TABLE 9

| | | L-lysine (g/L) | | | |
|---|---|---|---|---|---|
| | Strain | Batch 1 | Batch 2 | Batch 3 | Mean |
| Control | KCCM10770P | 47.5 | 48.1 | 47.9 | 47.8 |
| 1 | KCCM10770P::SigA(D136G, T281S) | 51.1 | 51.6 | 52.1 | 51.6 |

TABLE 9-continued

| | Strain | L-lysine (g/L) | | | |
| --- | --- | --- | --- | --- | --- |
| | | Batch 1 | Batch 2 | Batch 3 | Mean |
| 2 | KCCM10770P::SigA(L381R) | 52.6 | 50.9 | 52.1 | 51.9 |
| 3 | KCCM10770P::SigA(M455V) | 55.1 | 54.3 | 54.8 | 54.7 |
| 4 | KCCM10770P::SigA(S488T) | 52.1 | 52.4 | 51.9 | 52.1 |
| 5 | KCCM10770P::SigA(L447H) | 56.9 | 57.6 | 57.1 | 57.2 |
| 6 | KCCM10770P::SigA(A268S) | 50.5 | 50.1 | 49.9 | 50.2 |
| 7 | KCCM10770P::SigA(L451I, Q491R) | 55.3 | 54.9 | 54.1 | 54.8 |
| 8 | KCCM10770P::SigA(Q429R) | 52.4 | 52.3 | 50.9 | 51.9 |
| 9 | KCCM10770P::SigA(I254N) | 55.9 | 55.4 | 54.1 | 55.1 |
| 10 | KCCM10770P::SigA(K483R) | 51.9 | 51.3 | 51.5 | 51.6 |
| 11 | KCCM10770P::SigA(K479R) | 51 | 51.7 | 52.1 | 51.6 |
| Control | KCCM10770P::SigA(A414V) | 48.9 | 49.5 | 50.1 | 49.5 |

As a result, the 11 kinds of strains introduced with novel mutations showed a maximum increase of 20% in L-lysine production compared to that of the parent strain, and also showed an increase of about 16% in L-lysine production compared to that of KFCC10770::SigA(A414V), which is a strain introduced with the SigAA414V mutation reported previously.

Example 10: Preparation of CJ3P Strain Introduced with SigA-Modified Polypeptide for Strains Having L-Lysine Producibility in High Concentration and Comparison of their L-Lysine Productivities To confirm the effect in other strains of the genus *Corynebacterium glutamicum*, the strains in which SigA modifications were respectively introduced to *Corynebacterium glutamicum* CJ3P (Binder et al. *Genome Biology* 2012, 13: R40) having L-lysine producibility were prepared in the same manner as in Example 7. These strains were named as CJ3P::SigA(D136G, T281S), CJ3P::SigA(L381R), CJ3P::SigA(M455V), CJ3P::SigA(S488T), CJ3P::SigA(I254N), CJ3P::SigA(A268S), CJ3P::SigA(L451I, Q491R), CJ3P::SigA(Q429R), CJ3P::SigA(L447H), CJ3P::SigA(K483R), and CJ3P::SigA(K479R), respectively. Additionally, the strain introduced with the SigA(A414V) mutation, reported previously, was prepared and named as "CJ3P::SigA(A414V)". CJ3P is a *Corynebacterium glutamicum* strain, which has L-lysine producibility by the introduction of 3 kinds of mutations to the wild-type of the microorganism based on the known technology.

The strains were cultured in the same manner as in Example 4 and their L-lysine concentrations were analyzed. The results are shown in Table 10 below.

TABLE 10

| | Strain | L-lysine (g/L) | | | |
| --- | --- | --- | --- | --- | --- |
| | | Batch 1 | Batch 2 | Batch 3 | Mean |
| Control | CJ3P | 8.2 | 8.3 | 8.0 | 8.2 |
| 1 | CJ3P::SigA(D136G, T281S) | 9.0 | 8.8 | 8.9 | 8.9 |
| 2 | CJ3P::SigA(L381R) | 8.7 | 8.9 | 8.5 | 8.7 |
| 3 | CJ3P::SigA(M455V) | 9.3 | 9.5 | 9.1 | 9.3 |
| 4 | CJ3P::SigA(S488T) | 9.0 | 9.1 | 8.8 | 9.0 |
| 5 | CJ3P::SigA(L447H) | 9.8 | 10.1 | 9.5 | 9.8 |
| 6 | CJ3P::SigA(A268S) | 8.5 | 8.7 | 8.9 | 8.7 |
| 7 | CJ3P::SigA(L451I, Q491R) | 9.1 | 9.0 | 8.8 | 9.0 |
| 8 | CJ3P::SigA(Q429R) | 8.9 | 8.8 | 9.0 | 8.9 |
| 9 | CJ3P::SigA (I254N) | 9.1 | 9.7 | 9.5 | 9.4 |
| 10 | CJ3P::SigA(K483R) | 8.8 | 9.1 | 8.5 | 8.8 |
| 11 | CJ3P::SigA(K479R) | 8.6 | 8.9 | 8.8 | 8.8 |
| Control | CJ3P::SigA(A414V) | 8.5 | 8.4 | 8.6 | 8.5 |

As a result, the 11 kinds of strains introduced with novel mutations showed a maximum increase of 20% in L-lysine production compared to that of the parent strain, and also showed an increase of about 15% in L-lysine production compared to that of CJ3P::SigA(A414V), which is a strain introduced with the SigAA414V mutation reported previously.

Summarizing the above results, the 11 novel modified polypeptides having SigA activity obtained in the present disclosure (i.e., SigA(D136G, T281S), SigA(L381R), SigA(M455V), SigA(S488T), SigA(I254N), SigA(A268S), SigA(L451I, Q491R), SigA(Q429R), SigA(L447H), SigA(K483R), and SigA(K479R)) were shown to have an excellent effect on the improvement of L-lysine production, respectively, in various microorganisms of the genus *Corynebacterium*, and these results suggest that the modified polypeptides have an excellent effect on the improvement of L-lysine production compared to the modified SigA(A414V), which was reported previously.

From the foregoing, a skilled person in the art to which the present disclosure pertains will be able to understand that the present disclosure may be embodied in other specific forms without modifying the technical concepts or essential characteristics of the present disclosure. In this regard, the exemplary embodiments disclosed herein are only for illustrative purposes and should not be construed as limiting the scope of the present disclosure. On the contrary, the present disclosure is intended to cover not only the exemplary embodiments but also various alternatives, modifications, equivalents, and other embodiments that may be included within the spirit and scope of the present disclosure as defined by the appended claims.

The invention claimed is:

1. A modified polypeptide having RNA polymerase sigma factor A activity and the amino acid sequence set forth in SEQ ID NO: 2 but with one or two amino acid substitutions, wherein at least one of the one or two amino acid substitutions is selected from the group consisting of a substitution of the 136$^{th}$ amino acid with glycine; a substitution of the 254$^{th}$ amino acid with asparagine; a substitution of the 268$^{th}$ amino acid with serine; a substitution of the 281$^{st}$ amino acid with serine; a substitution of the 381$^{st}$ amino acid with arginine; a substitution of the 429$^{th}$ amino acid with arginine; a substitution of the 447$^{th}$ amino acid with histidine; a substitution of the 451$^{st}$ amino acid with isoleucine; a substitution of the 455$^{th}$ amino acid with valine; a substitution of the 479$^{th}$ amino acid with arginine; a substitution of the 483$^{rd}$ amino acid with arginine; a substitution of the 488$^{th}$ amino acid with threonine; and a substitution of the 491$^{st}$ amino acid with arginine.

2. The modified polypeptide according to claim 1, wherein the modified polypeptide has an amino acid sequence selected from the group consisting of the amino acid sequences set forth in SEQ ID NOS: 12 to 22.

3. A polynucleotide encoding the modified polypeptide of claim 1.

4. A host cell comprising the polynucleotide of claim 3.

5. A microorganism of the genus *Corynebacterium* having enhanced L-lysine producibility, comprising a modified polypeptide having RNA polymerase sigma factor A activity and the amino acid sequence set forth in SEQ ID NO: 2 but with one or two substitutions in SEQ ID NO:2, wherein at least one of the one or two substitutions is selected from the group consisting of a substitution of the 136$^{th}$ amino acid with glycine; a substitution of the 254$^{th}$ amino acid with asparagine; a substitution of the 268$^{th}$ amino acid with serine; a substitution of the 281$^{st}$ amino acid with serine; a substitution of the 381$^{st}$ amino acid with arginine; a substitution of the 429$^{th}$ amino acid with arginine; a substitution of the 447$^{th}$ amino acid with histidine; a substitution of the 451$^{st}$ amino acid with isoleucine; a substitution of the 455$^{th}$ amino acid with valine; a substitution of the 479$^{th}$ amino acid with arginine; a substitution of the 483$^{rd}$ amino acid with arginine; a substitution of the 488$^{th}$ amino acid with threonine; and a substitution of the 491$^{st}$ amino acid with arginine.

6. The microorganism according to claim 5, wherein the microorganism is *Corynebacterium glutamicum*.

7. A method for producing L-lysine, comprising:
(a) culturing the microorganism according to claim 5 in a medium; and
(b) recovering L-lysine from the cultured microorganism or the cultured medium.

* * * * *

SEQUENCE LISTING

<160> NUMBER OF SEQ ID NOS: 22

<210> SEQ ID NO 1
<211> LENGTH: 1497
<212> TYPE: DNA
<213> ORGANISM: Corynebacterium glutamicum

<400> SEQUENCE: 1

```
gtggagagca gcatggtaga aaacaacgta gcaaaaaaga cggtcgctaa aaagaccgca      60
cgcaagaccg cacgcaaagc agccccgcgc gtggcaaccc cattgggagt cgcatctgag     120
```

```
tctcccattt cggccacccc tgcgcgcagc atcgatggaa cctcaacccc tgttgaagct      180
gctgacacca tagagaccac cgcccctgca gcgaaggctc ctgcggccaa ggctcccgct      240
aaaaaggttg ccaagaagac agctcgcaag gcacctgcga aaaagactgt cgccaagaaa      300
gccacaaccg ccaaggctgc acctgcaact gccaaggacg aaaacgcacc tgttgatgac      360
gacgaggaga acctcgctca ggatgaacag gacttcgacg gcgatgactt cgtagacggc      420
atcgaagacg aagaagatga agacggcgtc gaagccctcg gtgaagaaag cgaagacgac      480
gaagaggacg gctcatccgt ttgggatgaa gacgaatccg caaccctgcg tcaggcacgt      540
aaagatgccg agctcaccgc ttccgccgac tctgttcgcg cttacctgaa gcaaatcggt      600
aaagttgccc tgctgaacgc tgaacaggaa gtctccctgg caaagcgcat cgaagcaggc      660
ctttacgcca cccaccgcat ggaggaaatg aagaagcttt cgcagccggt gacaaggac       720 gcgaaactca ccccagccgt caagcgtgac ctccgcgcca tcgctcgtga cggccgcaag      780
gcgaaaaacc acctcctgga agccaacctt cgtctggttg tctccctggc aaagcgctac      840
accggccgtg gcatggcatt cctggacctc atccaggaag caacctcgg tctgattcgt       900 gccgtagaga agttcgacta ctccaagggc tacaagttct ccacctacgc aacctggtgg      960
atccgtcagg caatcacccg cgccatggcc gaccaagcac gaaccatccg tatcccagtc      1020
cacatggttg aagtgatcaa caaacttggt cgcatccaac gtgaactcct tcaggaactc      1080
ggccgcgaac caaccccaca ggaactgtcc aaagaaatgg acatctccga ggaaaaggta      1140
ctggaaatcc agcagtacgc ccgcgaacca atctccctgg accaaaccat cggcgacgaa      1200
ggcgacagcc agctcggcga cttcatcgaa gactccgaag ccgtcgtcgc agtcgacgcc      1260
gtctcattca ccctgctgca agaccagcta caggacgtcc tagagaccct ctccgaacgt      1320
gaagccggcg tggttaaact ccgcttcgga ctcaccgacg gaatgccacg cactttagac      1380
gaaatcggcc aagtttacgg tgtcacccgt gagcgcatcc gccagattga gtccaagacc      1440
atgtctaagc tgcgccaccc catcacgctcc caggtccttc gcgactacct ggactaa       1497
```

<210> SEQ ID NO 2
<211> LENGTH: 498
<212> TYPE: PRT
<213> ORGANISM: Corynebacterium glutamicum

<400> SEQUENCE: 2

```
Met Glu Ser Ser Met Val Glu Asn Asn Val Ala Lys Lys Thr Val Ala
1               5                   10                  15

Lys Lys Thr Ala Arg Lys Thr Ala Arg Lys Ala Ala Pro Arg Val Ala
            20                  25                  30

Thr Pro Leu Gly Val Ala Ser Glu Ser Pro Ile Ser Ala Thr Pro Ala
        35                  40                  45

Arg Ser Ile Asp Gly Thr Ser Thr Pro Val Glu Ala Ala Asp Thr Ile
    50                  55                  60

Glu Thr Thr Ala Pro Ala Ala Lys Ala Pro Ala Ala Lys Ala Pro Ala
65                  70                  75                  80

Lys Lys Val Ala Lys Lys Thr Ala Arg Lys Ala Pro Ala Lys Lys Thr
                85                  90                  95

Val Ala Lys Lys Ala Thr Thr Ala Lys Ala Ala Pro Ala Thr Ala Lys
            100                 105                 110

Asp Glu Asn Ala Pro Val Asp Asp Glu Glu Asn Leu Ala Gln Asp
        115                 120                 125
```

```
Glu Gln Asp Phe Asp Gly Asp Phe Val Asp Gly Ile Glu Asp Glu
    130                 135                 140
Glu Asp Glu Asp Gly Val Glu Ala Leu Gly Glu Glu Ser Glu Asp Asp
145                 150                 155                 160
Glu Glu Asp Gly Ser Ser Val Trp Asp Glu Asp Ser Ala Thr Leu
                165                 170                 175
Arg Gln Ala Arg Lys Asp Ala Glu Leu Thr Ala Ser Ala Asp Ser Val
                180                 185                 190
Arg Ala Tyr Leu Lys Gln Ile Gly Lys Val Ala Leu Leu Asn Ala Glu
                195                 200                 205
Gln Glu Val Ser Leu Ala Lys Arg Ile Glu Ala Gly Leu Tyr Ala Thr
210                 215                 220
His Arg Met Glu Glu Met Glu Glu Ala Phe Ala Ala Gly Asp Lys Asp
225                 230                 235                 240
Ala Lys Leu Thr Pro Ala Val Lys Arg Asp Leu Arg Ala Ile Ala Arg
                245                 250                 255
Asp Gly Arg Lys Ala Lys Asn His Leu Leu Glu Ala Asn Leu Arg Leu
                260                 265                 270
Val Val Ser Leu Ala Lys Arg Tyr Thr Gly Arg Gly Met Ala Phe Leu
                275                 280                 285
Asp Leu Ile Gln Glu Gly Asn Leu Gly Leu Ile Arg Ala Val Glu Lys
                290                 295                 300
Phe Asp Tyr Ser Lys Gly Tyr Lys Phe Ser Thr Tyr Ala Thr Trp Trp
305                 310                 315                 320
Ile Arg Gln Ala Ile Thr Arg Ala Met Ala Asp Gln Ala Arg Thr Ile
                325                 330                 335
Arg Ile Pro Val His Met Val Glu Val Ile Asn Lys Leu Gly Arg Ile
                340                 345                 350
Gln Arg Glu Leu Leu Gln Leu Gly Arg Glu Pro Thr Pro Gln Glu
                355                 360                 365
Leu Ser Lys Glu Met Asp Ile Ser Glu Glu Lys Val Leu Glu Ile Gln
                370                 375                 380
Gln Tyr Ala Arg Glu Pro Ile Ser Leu Asp Gln Thr Ile Gly Asp Glu
385                 390                 395                 400
Gly Asp Ser Gln Leu Gly Asp Phe Ile Glu Asp Ser Glu Ala Val Val
                405                 410                 415
Ala Val Asp Ala Val Ser Phe Thr Leu Leu Gln Asp Gln Leu Gln Asp
                420                 425                 430
Val Leu Glu Thr Leu Ser Glu Arg Glu Ala Gly Val Val Lys Leu Arg
                435                 440                 445
Phe Gly Leu Thr Asp Gly Met Pro Arg Thr Leu Asp Glu Ile Gly Gln
                450                 455                 460
Val Tyr Gly Val Thr Arg Glu Arg Ile Arg Gln Ile Glu Ser Lys Thr
465                 470                 475                 480
Met Ser Lys Leu Arg His Pro Ser Arg Ser Gln Val Leu Arg Asp Tyr
                485                 490                 495
Leu Asp
```

<210> SEQ ID NO 3
<211> LENGTH: 19
<212> TYPE: DNA
<213> ORGANISM: Artificial Sequence
<220> FEATURE:
<223> OTHER INFORMATION: Primer 1

```
<400> SEQUENCE: 3
gtggagagca gcatggtag                                                      19

<210> SEQ ID NO 4
<211> LENGTH: 19
<212> TYPE: DNA
<213> ORGANISM: Artificial Sequence
<220> FEATURE:
<223> OTHER INFORMATION: Primer 2

<400> SEQUENCE: 4
cgcagaggaa aacagtggc                                                      19

<210> SEQ ID NO 5
<211> LENGTH: 16
<212> TYPE: DNA
<213> ORGANISM: Artificial Sequence
<220> FEATURE:
<223> OTHER INFORMATION: Primer 3

<400> SEQUENCE: 5
aacagctatg accatg                                                         16

<210> SEQ ID NO 6
<211> LENGTH: 27
<212> TYPE: DNA
<213> ORGANISM: Artificial Sequence
<220> FEATURE:
<223> OTHER INFORMATION: Primer 4

<400> SEQUENCE: 6
aagaattcgt ggagagcagc atggtag                                             27

<210> SEQ ID NO 7
<211> LENGTH: 27
<212> TYPE: DNA
<213> ORGANISM: Artificial Sequence
<220> FEATURE:
<223> OTHER INFORMATION: Primer 5

<400> SEQUENCE: 7
aagtcgaccg cagaggaaaa cagtggc                                             27

<210> SEQ ID NO 8
<211> LENGTH: 37
<212> TYPE: DNA
<213> ORGANISM: Artificial Sequence
<220> FEATURE:
<223> OTHER INFORMATION: Primer 6

<400> SEQUENCE: 8
gcaggtcgac tctagactca ccccagccgt caagcgt                                  37

<210> SEQ ID NO 9
<211> LENGTH: 37
<212> TYPE: DNA
<213> ORGANISM: Artificial Sequence
<220> FEATURE:
<223> OTHER INFORMATION: Primer 7

<400> SEQUENCE: 9 ccgggggatcc tctagatcaa ggcgatgtcg gaaaatg                                  37
```

-continued

<210> SEQ ID NO 10
<211> LENGTH: 25
<212> TYPE: DNA
<213> ORGANISM: Artificial Sequence
<220> FEATURE:
<223> OTHER INFORMATION: Primer 8

<400> SEQUENCE: 10
aagactccga agtcgtcgtc gcagt                                               25

<210> SEQ ID NO 11
<211> LENGTH: 25
<212> TYPE: DNA
<213> ORGANISM: Artificial Sequence
<220> FEATURE:
<223> OTHER INFORMATION: Primer 9

<400> SEQUENCE: 11
actgcgacga cgacttcgga gtctt                                               25

<210> SEQ ID NO 12
<211> LENGTH: 498
<212> TYPE: PRT
<213> ORGANISM: Artificial Sequence
<220> FEATURE:
<223> OTHER INFORMATION: SigA variant

<400> SEQUENCE: 12

Met Glu Ser Ser Met Val Glu Asn Asn Val Ala Lys Lys Thr Val Ala
1               5                   10                  15

Lys Lys Thr Ala Arg Lys Thr Ala Arg Lys Ala Ala Pro Arg Val Ala
            20                  25                  30

Thr Pro Leu Gly Val Ala Ser Glu Ser Pro Ile Ser Ala Thr Pro Ala
        35                  40                  45

Arg Ser Ile Asp Gly Thr Ser Thr Pro Val Glu Ala Ala Asp Thr Ile
    50                  55                  60

Glu Thr Thr Ala Pro Ala Ala Lys Ala Pro Ala Lys Ala Pro Ala
65                  70                  75                  80

Lys Lys Val Ala Lys Lys Thr Ala Arg Lys Ala Pro Ala Lys Lys Thr
                85                  90                  95

Val Ala Lys Lys Ala Thr Thr Ala Lys Ala Pro Ala Thr Ala Lys
            100                 105                 110

Asp Glu Asn Ala Pro Val Asp Asp Glu Gly Asn Leu Ala Gln Asp
            115                 120                 125

Glu Gln Asp Phe Asp Gly Asp Gly Phe Val Asp Gly Ile Glu Asp Glu
    130                 135                 140

Glu Asp Glu Asp Gly Val Glu Ala Leu Gly Glu Ser Glu Asp
145                 150                 155                 160

Glu Glu Asp Gly Ser Ser Val Trp Asp Glu Asp Glu Ser Ala Thr Leu
                165                 170                 175

Arg Gln Ala Arg Lys Asp Ala Glu Leu Thr Ala Ser Ala Asp Ser Val
            180                 185                 190

Arg Ala Tyr Leu Lys Gln Ile Gly Lys Val Ala Leu Leu Asn Ala Glu
        195                 200                 205

Gln Glu Val Ser Leu Ala Lys Arg Ile Glu Ala Gly Leu Tyr Ala Thr
    210                 215                 220

His Arg Met Glu Glu Met Glu Glu Ala Phe Ala Ala Gly Asp Lys Asp
225                 230                 235                 240

Ala Lys Leu Thr Pro Ala Val Lys Arg Asp Leu Arg Ala Ile Ala Arg
                245                 250                 255

Asp Gly Arg Lys Ala Lys Asn His Leu Leu Glu Ala Asn Leu Arg Leu
            260                 265                 270

Val Val Ser Leu Ala Lys Arg Tyr Ser Gly Arg Gly Met Ala Phe Leu
        275                 280                 285

Asp Leu Ile Gln Glu Gly Asn Leu Gly Leu Ile Arg Ala Val Glu Lys
    290                 295                 300

Phe Asp Tyr Ser Lys Gly Tyr Lys Phe Ser Thr Tyr Ala Thr Trp Trp
305                 310                 315                 320

Ile Arg Gln Ala Ile Thr Arg Ala Met Ala Asp Gln Ala Arg Thr Ile
                325                 330                 335

Arg Ile Pro Val His Met Val Glu Val Ile Asn Lys Leu Gly Arg Ile
            340                 345                 350

Gln Arg Glu Leu Leu Gln Leu Gly Arg Glu Pro Thr Pro Gln Glu
        355                 360                 365

Leu Ser Lys Glu Met Asp Ile Ser Glu Glu Lys Val Leu Glu Ile Gln
    370                 375                 380

Gln Tyr Ala Arg Glu Pro Ile Ser Leu Asp Gln Thr Ile Gly Asp Glu
385                 390                 395                 400

Gly Asp Ser Gln Leu Gly Asp Phe Ile Glu Asp Ser Glu Ala Val Val
                405                 410                 415

Ala Val Asp Ala Val Ser Phe Thr Leu Leu Gln Asp Gln Leu Gln Asp
            420                 425                 430

Val Leu Glu Thr Leu Ser Glu Arg Glu Ala Gly Val Val Lys Leu Arg
        435                 440                 445

Phe Gly Leu Thr Asp Gly Met Pro Arg Thr Leu Asp Glu Ile Gly Gln
    450                 455                 460

Val Tyr Gly Val Thr Arg Glu Arg Ile Arg Gln Ile Glu Ser Lys Thr
465                 470                 475                 480

Met Ser Lys Leu Arg His Pro Ser Arg Ser Gln Val Leu Arg Asp Tyr
                485                 490                 495

Leu Asp

<210> SEQ ID NO 13
<211> LENGTH: 498
<212> TYPE: PRT
<213> ORGANISM: Artificial Sequence
<220> FEATURE:
<223> OTHER INFORMATION: SigA variant

<400> SEQUENCE: 13

Met Glu Ser Ser Met Val Glu Asn Asn Val Ala Lys Lys Thr Val Ala
1               5                   10                  15

Lys Lys Thr Ala Arg Lys Thr Ala Arg Lys Ala Ala Pro Arg Val Ala
            20                  25                  30

Thr Pro Leu Gly Val Ala Ser Glu Ser Pro Ile Ser Ala Thr Pro Ala
        35                  40                  45

Arg Ser Ile Asp Gly Thr Ser Thr Pro Val Glu Ala Ala Asp Thr Ile
    50                  55                  60

Glu Thr Thr Ala Pro Ala Ala Lys Ala Pro Ala Lys Ala Pro Ala
65                  70                  75                  80

Lys Lys Val Ala Lys Lys Thr Ala Arg Lys Ala Pro Ala Lys Lys Thr
                85                  90                  95

```
Val Ala Lys Lys Ala Thr Thr Ala Lys Ala Pro Ala Thr Ala Lys
            100                 105                 110

Asp Glu Asn Ala Pro Val Asp Asp Glu Glu Asn Leu Ala Gln Asp
            115                 120                 125

Glu Gln Asp Phe Asp Gly Asp Asp Phe Val Asp Gly Ile Glu Asp Glu
            130                 135                 140

Glu Asp Glu Asp Gly Val Glu Ala Leu Gly Glu Ser Glu Asp Asp
145                 150                 155                 160

Glu Glu Asp Gly Ser Ser Val Trp Asp Glu Asp Glu Ser Ala Thr Leu
                165                 170                 175

Arg Gln Ala Arg Lys Asp Ala Glu Leu Thr Ala Ser Ala Asp Ser Val
            180                 185                 190

Arg Ala Tyr Leu Lys Gln Ile Gly Lys Val Ala Leu Leu Asn Ala Glu
            195                 200                 205

Gln Glu Val Ser Leu Ala Lys Arg Ile Glu Ala Gly Leu Tyr Ala Thr
            210                 215                 220

His Arg Met Glu Glu Met Glu Glu Ala Phe Ala Ala Gly Asp Lys Asp
225                 230                 235                 240

Ala Lys Leu Thr Pro Ala Val Lys Arg Asp Leu Arg Ala Ile Ala Arg
            245                 250                 255

Asp Gly Arg Lys Ala Lys Asn His Leu Leu Glu Ala Asn Leu Arg Leu
            260                 265                 270

Val Val Ser Leu Ala Lys Arg Tyr Thr Gly Arg Gly Met Ala Phe Leu
            275                 280                 285

Asp Leu Ile Gln Glu Gly Asn Leu Gly Leu Ile Arg Ala Val Glu Lys
            290                 295                 300

Phe Asp Tyr Ser Lys Gly Tyr Lys Phe Ser Thr Tyr Ala Thr Trp Trp
305                 310                 315                 320

Ile Arg Gln Ala Ile Thr Arg Ala Met Ala Asp Gln Ala Arg Thr Ile
            325                 330                 335

Arg Ile Pro Val His Met Val Glu Val Ile Asn Lys Leu Gly Arg Ile
            340                 345                 350

Gln Arg Glu Leu Leu Gln Glu Leu Gly Arg Glu Pro Thr Pro Gln Glu
            355                 360                 365

Leu Ser Lys Glu Met Asp Ile Ser Glu Glu Lys Val Arg Glu Ile Gln
            370                 375                 380

Gln Tyr Ala Arg Glu Pro Ile Ser Leu Asp Gln Thr Ile Gly Asp Glu
385                 390                 395                 400

Gly Asp Ser Gln Leu Gly Asp Phe Ile Glu Asp Ser Glu Ala Val Val
                405                 410                 415

Ala Val Asp Ala Val Ser Phe Thr Leu Leu Gln Asp Gln Leu Gln Asp
            420                 425                 430

Val Leu Glu Thr Leu Ser Glu Arg Glu Ala Gly Val Val Lys Leu Arg
            435                 440                 445

Phe Gly Leu Thr Asp Gly Met Pro Arg Thr Leu Asp Glu Ile Gly Gln
            450                 455                 460

Val Tyr Gly Val Thr Arg Glu Arg Ile Arg Gln Ile Glu Ser Lys Thr
465                 470                 475                 480

Met Ser Lys Leu Arg His Pro Ser Arg Ser Gln Val Leu Arg Asp Tyr
            485                 490                 495

Leu Asp
```

<210> SEQ ID NO 14
<211> LENGTH: 498
<212> TYPE: PRT
<213> ORGANISM: Artificial Sequence
<220> FEATURE:
<223> OTHER INFORMATION: SigA variant

<400> SEQUENCE: 14

```
Met Glu Ser Ser Met Val Glu Asn Asn Val Ala Lys Thr Val Ala
1               5                   10                  15

Lys Lys Thr Ala Arg Lys Thr Ala Arg Lys Ala Ala Pro Arg Val Ala
                20                  25                  30

Thr Pro Leu Gly Val Ala Ser Glu Ser Pro Ile Ser Ala Thr Pro Ala
            35                  40                  45

Arg Ser Ile Asp Gly Thr Ser Thr Pro Val Glu Ala Ala Asp Thr Ile
    50                  55                  60

Glu Thr Thr Ala Pro Ala Ala Lys Ala Pro Ala Ala Lys Ala Pro Ala
65                  70                  75                  80

Lys Lys Val Ala Lys Lys Thr Ala Arg Lys Ala Pro Ala Lys Lys Thr
                85                  90                  95

Val Ala Lys Lys Ala Thr Thr Ala Lys Ala Ala Pro Ala Thr Ala Lys
                100                 105                 110

Asp Glu Asn Ala Pro Val Asp Asp Glu Glu Asn Leu Ala Gln Asp
            115                 120                 125

Glu Gln Asp Phe Asp Gly Asp Asp Phe Val Asp Gly Ile Glu Asp Glu
            130                 135                 140

Glu Asp Glu Asp Gly Val Glu Ala Leu Gly Glu Ser Glu Asp Asp
145                 150                 155                 160

Glu Glu Asp Gly Ser Ser Val Trp Asp Glu Asp Glu Ser Ala Thr Leu
                165                 170                 175

Arg Gln Ala Arg Lys Asp Ala Glu Leu Thr Ala Ser Ala Asp Ser Val
                180                 185                 190

Arg Ala Tyr Leu Lys Gln Ile Gly Lys Val Ala Leu Leu Asn Ala Glu
        195                 200                 205

Gln Glu Val Ser Leu Ala Lys Arg Ile Glu Ala Gly Leu Tyr Ala Thr
210                 215                 220

His Arg Met Glu Glu Met Glu Glu Ala Phe Ala Ala Gly Asp Lys Asp
225                 230                 235                 240

Ala Lys Leu Thr Pro Ala Val Lys Arg Asp Leu Arg Ala Ile Ala Arg
                245                 250                 255

Asp Gly Arg Lys Ala Lys Asn His Leu Leu Glu Ala Asn Leu Arg Leu
            260                 265                 270

Val Val Ser Leu Ala Lys Arg Tyr Thr Gly Arg Gly Met Ala Phe Leu
        275                 280                 285

Asp Leu Ile Gln Glu Gly Asn Leu Gly Leu Ile Arg Ala Val Glu Lys
    290                 295                 300

Phe Asp Tyr Ser Lys Gly Tyr Lys Phe Ser Thr Tyr Ala Thr Trp Trp
305                 310                 315                 320

Ile Arg Gln Ala Ile Thr Arg Ala Met Ala Asp Gln Ala Arg Thr Ile
                325                 330                 335

Arg Ile Pro Val His Met Val Glu Val Ile Asn Lys Leu Gly Arg Ile
            340                 345                 350

Gln Arg Glu Leu Leu Gln Glu Leu Gly Arg Glu Pro Thr Pro Gln Glu
        355                 360                 365
```

```
Leu Ser Lys Glu Met Asp Ile Ser Glu Glu Lys Val Leu Glu Ile Gln
        370                 375                 380

Gln Tyr Ala Arg Glu Pro Ile Ser Leu Asp Gln Thr Ile Gly Asp Glu
385                 390                 395                 400

Gly Asp Ser Gln Leu Gly Asp Phe Ile Glu Asp Ser Glu Ala Val Val
                405                 410                 415

Ala Val Asp Ala Val Ser Phe Thr Leu Leu Gln Asp Gln Leu Gln Asp
                420                 425                 430

Val Leu Glu Thr Leu Ser Glu Arg Glu Ala Gly Val Val Lys Leu Arg
                435                 440                 445

Phe Gly Leu Thr Asp Gly Val Pro Arg Thr Leu Asp Glu Ile Gly Gln
450                 455                 460

Val Tyr Gly Val Thr Arg Glu Arg Ile Arg Gln Ile Glu Ser Lys Thr
465                 470                 475                 480

Met Ser Lys Leu Arg His Pro Ser Arg Ser Gln Val Leu Arg Asp Tyr
                485                 490                 495

Leu Asp

<210> SEQ ID NO 15
<211> LENGTH: 498
<212> TYPE: PRT
<213> ORGANISM: Artificial Sequence
<220> FEATURE:
<223> OTHER INFORMATION: SigA variant

<400> SEQUENCE: 15

Met Glu Ser Ser Met Val Glu Asn Asn Val Ala Lys Lys Thr Val Ala
1               5                   10                  15

Lys Lys Thr Ala Arg Lys Thr Ala Arg Lys Ala Ala Pro Arg Val Ala
                20                  25                  30

Thr Pro Leu Gly Val Ala Ser Glu Ser Pro Ile Ser Ala Thr Pro Ala
                35                  40                  45

Arg Ser Ile Asp Gly Thr Ser Thr Pro Val Glu Ala Ala Asp Thr Ile
        50                  55                  60

Glu Thr Thr Ala Pro Ala Ala Lys Ala Pro Ala Ala Lys Ala Pro Ala
65                  70                  75                  80

Lys Lys Val Ala Lys Lys Thr Ala Arg Lys Ala Pro Ala Lys Lys Thr
                85                  90                  95

Val Ala Lys Lys Ala Thr Thr Ala Lys Ala Ala Pro Ala Thr Ala Lys
                100                 105                 110

Asp Glu Asn Ala Pro Val Asp Asp Glu Glu Asn Leu Ala Gln Asp
                115                 120                 125

Glu Gln Asp Phe Asp Gly Asp Asp Phe Val Asp Gly Ile Glu Asp Glu
        130                 135                 140

Glu Asp Glu Asp Gly Val Glu Ala Leu Gly Glu Glu Ser Glu Asp Asp
145                 150                 155                 160

Glu Glu Asp Gly Ser Ser Val Trp Asp Glu Asp Glu Ser Ala Thr Leu
                165                 170                 175

Arg Gln Ala Arg Lys Asp Ala Glu Leu Thr Ala Ser Ala Asp Ser Val
                180                 185                 190

Arg Ala Tyr Leu Lys Gln Ile Gly Lys Val Ala Leu Leu Asn Ala Glu
                195                 200                 205

Gln Glu Val Ser Leu Ala Lys Arg Ile Glu Ala Gly Leu Tyr Ala Thr
        210                 215                 220
```

His Arg Met Glu Glu Met Glu Glu Ala Phe Ala Ala Gly Asp Lys Asp
225                 230                 235                 240

Ala Lys Leu Thr Pro Ala Val Lys Arg Asp Leu Arg Ala Ile Ala Arg
            245                 250                 255

Asp Gly Arg Lys Ala Lys Asn His Leu Leu Glu Ala Asn Leu Arg Leu
        260                 265                 270

Val Val Ser Leu Ala Lys Arg Tyr Thr Gly Arg Gly Met Ala Phe Leu
    275                 280                 285

Asp Leu Ile Gln Glu Gly Asn Leu Gly Leu Ile Arg Ala Val Glu Lys
290                 295                 300

Phe Asp Tyr Ser Lys Gly Tyr Lys Phe Ser Thr Tyr Ala Thr Trp Trp
305                 310                 315                 320

Ile Arg Gln Ala Ile Thr Arg Ala Met Ala Asp Gln Ala Arg Thr Ile
            325                 330                 335

Arg Ile Pro Val His Met Val Glu Val Ile Asn Lys Leu Gly Arg Ile
        340                 345                 350

Gln Arg Glu Leu Leu Gln Glu Leu Gly Arg Glu Pro Thr Pro Gln Glu
    355                 360                 365

Leu Ser Lys Glu Met Asp Ile Ser Glu Glu Lys Val Leu Glu Ile Gln
370                 375                 380

Gln Tyr Ala Arg Glu Pro Ile Ser Leu Asp Gln Thr Ile Gly Asp Glu
385                 390                 395                 400

Gly Asp Ser Gln Leu Gly Asp Phe Ile Glu Ser Glu Ala Val Val
            405                 410                 415

Ala Val Asp Ala Val Ser Phe Thr Leu Leu Gln Asp Gln Leu Gln Asp
        420                 425                 430

Val Leu Glu Thr Leu Ser Glu Arg Glu Ala Gly Val Val Lys Leu Arg
    435                 440                 445

Phe Gly Leu Thr Asp Gly Met Pro Arg Thr Leu Asp Glu Ile Gly Gln
450                 455                 460

Val Tyr Gly Val Thr Arg Glu Arg Ile Arg Gln Ile Glu Ser Lys Thr
465                 470                 475                 480

Met Ser Lys Leu Arg His Pro Thr Arg Ser Gln Val Leu Arg Asp Tyr
            485                 490                 495

Leu Asp

<210> SEQ ID NO 16
<211> LENGTH: 498
<212> TYPE: PRT
<213> ORGANISM: Artificial Sequence
<220> FEATURE:
<223> OTHER INFORMATION: SigA variant

<400> SEQUENCE: 16

Met Glu Ser Ser Met Val Glu Asn Asn Val Ala Lys Lys Thr Val Ala
1               5                   10                  15

Lys Lys Thr Ala Arg Lys Thr Ala Arg Lys Ala Ala Pro Arg Val Ala
            20                  25                  30

Thr Pro Leu Gly Val Ala Ser Glu Ser Pro Ile Ser Ala Thr Pro Ala
        35                  40                  45

Arg Ser Ile Asp Gly Thr Ser Thr Pro Val Glu Ala Ala Asp Thr Ile
    50                  55                  60

Glu Thr Thr Ala Pro Ala Ala Lys Ala Pro Ala Ala Lys Ala Pro Ala
65                  70                  75                  80

```
Lys Lys Val Ala Lys Lys Thr Ala Arg Lys Ala Pro Ala Lys Lys Thr
                85                  90                  95

Val Ala Lys Lys Ala Thr Thr Ala Lys Ala Ala Pro Ala Thr Ala Lys
            100                 105                 110

Asp Glu Asn Ala Pro Val Asp Asp Glu Glu Asn Leu Ala Gln Asp
        115                 120                 125

Glu Gln Asp Phe Asp Gly Asp Phe Val Asp Gly Ile Glu Asp Glu
    130                 135                 140

Glu Asp Glu Asp Gly Val Glu Ala Leu Gly Glu Ser Glu Asp Asp
145                 150                 155                 160

Glu Glu Asp Gly Ser Ser Val Trp Asp Glu Asp Glu Ser Ala Thr Leu
                165                 170                 175

Arg Gln Ala Arg Lys Asp Ala Glu Leu Thr Ala Ser Ala Asp Ser Val
                180                 185                 190

Arg Ala Tyr Leu Lys Gln Ile Gly Lys Val Ala Leu Leu Asn Ala Glu
            195                 200                 205

Gln Glu Val Ser Leu Ala Lys Arg Ile Glu Ala Gly Leu Tyr Ala Thr
        210                 215                 220

His Arg Met Glu Glu Met Glu Glu Ala Phe Ala Ala Gly Asp Lys Asp
225                 230                 235                 240

Ala Lys Leu Thr Pro Ala Val Lys Arg Asp Leu Arg Ala Ile Ala Arg
                245                 250                 255

Asp Gly Arg Lys Ala Lys Asn His Leu Leu Glu Ala Asn Leu Arg Leu
            260                 265                 270

Val Val Ser Leu Ala Lys Arg Tyr Thr Gly Arg Gly Met Ala Phe Leu
        275                 280                 285

Asp Leu Ile Gln Glu Gly Asn Leu Gly Leu Ile Arg Ala Val Glu Lys
    290                 295                 300

Phe Asp Tyr Ser Lys Gly Tyr Lys Phe Ser Thr Tyr Ala Thr Trp Trp
305                 310                 315                 320

Ile Arg Gln Ala Ile Thr Arg Ala Met Ala Asp Gln Ala Arg Thr Ile
                325                 330                 335

Arg Ile Pro Val His Met Val Glu Val Ile Asn Lys Leu Gly Arg Ile
            340                 345                 350

Gln Arg Glu Leu Leu Gln Glu Leu Gly Arg Glu Pro Thr Pro Gln Glu
        355                 360                 365

Leu Ser Lys Glu Met Asp Ile Ser Glu Glu Lys Val Leu Glu Ile Gln
    370                 375                 380

Gln Tyr Ala Arg Glu Pro Ile Ser Leu Asp Gln Thr Ile Gly Asp Glu
385                 390                 395                 400

Gly Asp Ser Gln Leu Gly Asp Phe Ile Glu Asp Ser Glu Ala Val Val
                405                 410                 415

Ala Val Asp Ala Val Ser Phe Thr Leu Leu Gln Asp Gln Leu Gln Asp
            420                 425                 430

Val Leu Glu Thr Leu Ser Glu Arg Glu Ala Gly Val Val Lys His Arg
        435                 440                 445

Phe Gly Leu Thr Asp Gly Met Pro Arg Thr Leu Asp Glu Ile Gly Gln
    450                 455                 460

Val Tyr Gly Val Thr Arg Glu Arg Ile Arg Gln Ile Glu Ser Lys Thr
465                 470                 475                 480

Met Ser Lys Leu Arg His Pro Ser Arg Ser Gln Val Leu Arg Asp Tyr
                485                 490                 495

Leu Asp
```

<210> SEQ ID NO 17
<211> LENGTH: 498
<212> TYPE: PRT
<213> ORGANISM: Artificial Sequence
<220> FEATURE:
<223> OTHER INFORMATION: SigA variant

<400> SEQUENCE: 17

```
Met Glu Ser Ser Met Val Glu Asn Asn Val Ala Lys Thr Val Ala
1               5                   10                  15

Lys Lys Thr Ala Arg Lys Thr Ala Arg Lys Ala Ala Pro Arg Val Ala
                20                  25                  30

Thr Pro Leu Gly Val Ala Ser Glu Ser Pro Ile Ser Ala Thr Pro Ala
            35                  40                  45

Arg Ser Ile Asp Gly Thr Ser Thr Pro Val Glu Ala Ala Asp Thr Ile
        50                  55                  60

Glu Thr Thr Ala Pro Ala Ala Lys Ala Pro Ala Ala Lys Ala Pro Ala
65                  70                  75                  80

Lys Lys Val Ala Lys Lys Thr Ala Arg Lys Ala Pro Ala Lys Lys Thr
                85                  90                  95

Val Ala Lys Lys Ala Thr Thr Ala Lys Ala Ala Pro Ala Thr Ala Lys
                100                 105                 110

Asp Glu Asn Ala Pro Val Asp Asp Glu Glu Asn Leu Ala Gln Asp
                115                 120                 125

Glu Gln Asp Phe Asp Gly Asp Asp Phe Val Asp Gly Ile Glu Asp Glu
    130                 135                 140

Glu Asp Glu Asp Gly Val Glu Ala Leu Gly Glu Ser Glu Asp Asp
145                 150                 155                 160

Glu Glu Asp Gly Ser Ser Val Trp Asp Glu Asp Ser Ala Thr Leu
                165                 170                 175

Arg Gln Ala Arg Lys Asp Ala Glu Leu Thr Ala Ser Ala Asp Ser Val
                180                 185                 190

Arg Ala Tyr Leu Lys Gln Ile Gly Lys Val Ala Leu Leu Asn Ala Glu
            195                 200                 205

Gln Glu Val Ser Leu Ala Lys Arg Ile Glu Ala Gly Leu Tyr Ala Thr
    210                 215                 220

His Arg Met Glu Glu Met Glu Glu Ala Phe Ala Ala Gly Asp Lys Asp
225                 230                 235                 240

Ala Lys Leu Thr Pro Ala Val Lys Arg Asp Leu Arg Ala Ile Ala Arg
                245                 250                 255

Asp Gly Arg Lys Ala Lys Asn His Leu Leu Glu Ser Asn Leu Arg Leu
            260                 265                 270

Val Val Ser Leu Ala Lys Arg Tyr Thr Gly Arg Gly Met Ala Phe Leu
        275                 280                 285

Asp Leu Ile Gln Glu Gly Asn Leu Gly Leu Ile Arg Ala Val Glu Lys
    290                 295                 300

Phe Asp Tyr Ser Lys Gly Tyr Lys Phe Ser Thr Tyr Ala Thr Trp Trp
305                 310                 315                 320

Ile Arg Gln Ala Ile Thr Arg Ala Met Ala Asp Gln Ala Arg Thr Ile
                325                 330                 335

Arg Ile Pro Val His Met Val Glu Val Ile Asn Lys Leu Gly Arg Ile
            340                 345                 350

Gln Arg Glu Leu Leu Gln Glu Leu Gly Arg Glu Pro Thr Pro Gln Glu
        355                 360                 365
```

-continued

```
Leu Ser Lys Glu Met Asp Ile Ser Glu Glu Lys Val Leu Glu Ile Gln
    370                 375                 380

Gln Tyr Ala Arg Glu Pro Ile Ser Leu Asp Gln Thr Ile Gly Asp Glu
385                 390                 395                 400

Gly Asp Ser Gln Leu Gly Asp Phe Ile Glu Asp Ser Glu Ala Val Val
                405                 410                 415

Ala Val Asp Ala Val Ser Phe Thr Leu Leu Gln Asp Gln Leu Gln Asp
            420                 425                 430

Val Leu Glu Thr Leu Ser Glu Arg Glu Ala Gly Val Val Lys Leu Arg
        435                 440                 445

Phe Gly Leu Thr Asp Gly Met Pro Arg Thr Leu Asp Glu Ile Gly Gln
    450                 455                 460

Val Tyr Gly Val Thr Arg Glu Arg Ile Arg Gln Ile Glu Ser Lys Thr
465                 470                 475                 480

Met Ser Lys Leu Arg His Pro Ser Arg Ser Gln Val Leu Arg Asp Tyr
                485                 490                 495

Leu Asp
```

<210> SEQ ID NO 18
<211> LENGTH: 498
<212> TYPE: PRT
<213> ORGANISM: Artificial Sequence
<220> FEATURE:
<223> OTHER INFORMATION: SigA variant

<400> SEQUENCE: 18

```
Met Glu Ser Ser Met Val Glu Asn Asn Val Ala Lys Lys Thr Val Ala
1               5                   10                  15

Lys Lys Thr Ala Arg Lys Thr Ala Arg Lys Ala Ala Pro Arg Val Ala
            20                  25                  30

Thr Pro Leu Gly Val Ala Ser Glu Ser Pro Ile Ser Ala Thr Pro Ala
        35                  40                  45

Arg Ser Ile Asp Gly Thr Ser Thr Pro Val Glu Ala Ala Asp Thr Ile
    50                  55                  60

Glu Thr Thr Ala Pro Ala Ala Lys Ala Pro Ala Ala Lys Ala Pro Ala
65                  70                  75                  80

Lys Lys Val Ala Lys Lys Thr Ala Arg Lys Ala Pro Ala Lys Lys Thr
                85                  90                  95

Val Ala Lys Lys Ala Thr Thr Ala Lys Ala Ala Pro Ala Thr Ala Lys
            100                 105                 110

Asp Glu Asn Ala Pro Val Asp Asp Glu Glu Asn Leu Ala Gln Asp
        115                 120                 125

Glu Gln Asp Phe Asp Gly Asp Asp Phe Val Asp Gly Ile Glu Asp Glu
    130                 135                 140

Glu Asp Glu Asp Gly Val Glu Ala Leu Gly Glu Glu Ser Glu Asp Asp
145                 150                 155                 160

Glu Glu Asp Gly Ser Ser Val Trp Asp Glu Asp Glu Ser Ala Thr Leu
                165                 170                 175

Arg Gln Ala Arg Lys Asp Ala Glu Leu Thr Ala Ser Ala Asp Ser Val
            180                 185                 190

Arg Ala Tyr Leu Lys Gln Ile Gly Lys Val Ala Leu Leu Asn Ala Glu
        195                 200                 205

Gln Glu Val Ser Leu Ala Lys Arg Ile Glu Ala Gly Leu Tyr Ala Thr
    210                 215                 220
```

His Arg Met Glu Glu Met Glu Glu Ala Phe Ala Ala Gly Asp Lys Asp
225                 230                 235                 240

Ala Lys Leu Thr Pro Ala Val Lys Arg Asp Leu Arg Ala Ile Ala Arg
            245                 250                 255

Asp Gly Arg Lys Ala Lys Asn His Leu Leu Glu Ala Asn Leu Arg Leu
        260                 265                 270

Val Val Ser Leu Ala Lys Arg Tyr Thr Gly Arg Gly Met Ala Phe Leu
    275                 280                 285

Asp Leu Ile Gln Glu Gly Asn Leu Gly Leu Ile Arg Ala Val Glu Lys
290                 295                 300

Phe Asp Tyr Ser Lys Gly Tyr Lys Phe Ser Thr Tyr Ala Thr Trp Trp
305                 310                 315                 320

Ile Arg Gln Ala Ile Thr Arg Ala Met Ala Asp Gln Ala Arg Thr Ile
            325                 330                 335

Arg Ile Pro Val His Met Val Glu Val Ile Asn Lys Leu Gly Arg Ile
        340                 345                 350

Gln Arg Glu Leu Leu Gln Glu Leu Gly Arg Glu Pro Thr Pro Gln Glu
    355                 360                 365

Leu Ser Lys Glu Met Asp Ile Ser Glu Glu Lys Val Leu Glu Ile Gln
370                 375                 380

Gln Tyr Ala Arg Glu Pro Ile Ser Leu Asp Gln Thr Ile Gly Asp Glu
385                 390                 395                 400

Gly Asp Ser Gln Leu Gly Asp Phe Ile Glu Ser Glu Ala Val Val
            405                 410                 415

Ala Val Asp Ala Val Ser Phe Thr Leu Leu Gln Asp Gln Leu Gln Asp
        420                 425                 430

Val Leu Glu Thr Leu Ser Arg Glu Ala Gly Val Val Lys Leu Arg
    435                 440                 445

Phe Gly Ile Thr Asp Gly Met Pro Arg Thr Leu Asp Glu Ile Gly Gln
450                 455                 460

Val Tyr Gly Val Thr Arg Glu Arg Ile Arg Gln Ile Glu Ser Lys Thr
465                 470                 475                 480

Met Ser Lys Leu Arg His Pro Ser Arg Ser Arg Val Leu Arg Asp Tyr
            485                 490                 495

Leu Asp

<210> SEQ ID NO 19
<211> LENGTH: 498
<212> TYPE: PRT
<213> ORGANISM: Artificial Sequence
<220> FEATURE:
<223> OTHER INFORMATION: SigA variant

<400> SEQUENCE: 19

Met Glu Ser Ser Met Val Glu Asn Asn Val Ala Lys Lys Thr Val Ala
1               5                   10                  15

Lys Lys Thr Ala Arg Lys Thr Ala Arg Lys Ala Ala Pro Arg Val Ala
            20                  25                  30

Thr Pro Leu Gly Val Ala Ser Glu Ser Pro Ile Ser Ala Thr Pro Ala
        35                  40                  45

Arg Ser Ile Asp Gly Thr Ser Thr Pro Val Gly Ala Ala Asp Thr Ile
    50                  55                  60

Glu Thr Thr Ala Pro Ala Ala Lys Ala Pro Ala Ala Lys Ala Pro Ala
65                  70                  75                  80

```
Lys Lys Val Ala Lys Thr Ala Arg Lys Ala Pro Ala Lys Lys Thr
                85                  90                  95

Val Ala Lys Lys Ala Thr Thr Ala Lys Ala Ala Pro Ala Thr Ala Lys
            100                 105                 110

Asp Glu Asn Ala Pro Val Asp Asp Glu Glu Asn Leu Ala Gln Asp
        115                 120                 125

Glu Gln Asp Phe Asp Gly Asp Phe Val Asp Gly Ile Glu Asp Glu
    130                 135                 140

Glu Asp Glu Asp Gly Val Glu Ala Leu Gly Glu Ser Glu Asp Asp
145                 150                 155                 160

Glu Glu Asp Gly Ser Ser Val Trp Asp Glu Asp Glu Ser Ala Thr Leu
                165                 170                 175

Arg Gln Ala Arg Lys Asp Ala Glu Leu Thr Ala Ser Ala Asp Ser Val
            180                 185                 190

Arg Ala Tyr Leu Lys Gln Ile Gly Lys Val Ala Leu Leu Asn Ala Glu
        195                 200                 205

Gln Glu Val Ser Leu Ala Lys Arg Ile Glu Ala Gly Leu Tyr Ala Thr
    210                 215                 220

His Arg Met Glu Glu Met Glu Glu Ala Phe Ala Ala Gly Asp Lys Asp
225                 230                 235                 240

Ala Lys Leu Thr Pro Ala Val Lys Arg Asp Leu Arg Ala Ile Ala Arg
                245                 250                 255

Asp Gly Arg Lys Ala Lys Asn His Leu Leu Glu Ala Asn Leu Arg Leu
            260                 265                 270

Val Val Ser Leu Ala Lys Arg Tyr Thr Gly Arg Gly Met Ala Phe Leu
        275                 280                 285

Asp Leu Ile Gln Glu Gly Asn Leu Gly Leu Ile Arg Ala Val Glu Lys
    290                 295                 300

Phe Asp Tyr Ser Lys Gly Tyr Lys Phe Ser Thr Tyr Ala Thr Trp Trp
305                 310                 315                 320

Ile Arg Gln Ala Ile Thr Arg Ala Met Ala Asp Gln Ala Arg Thr Ile
                325                 330                 335

Arg Ile Pro Val His Met Val Glu Val Ile Asn Lys Leu Gly Arg Ile
            340                 345                 350

Gln Arg Glu Leu Leu Gln Glu Leu Gly Arg Glu Pro Thr Pro Gln Glu
        355                 360                 365

Leu Ser Lys Glu Met Asp Ile Ser Glu Glu Lys Val Leu Glu Ile Gln
    370                 375                 380

Gln Tyr Ala Arg Glu Pro Ile Ser Leu Asp Gln Thr Ile Gly Asp Glu
385                 390                 395                 400

Gly Asp Ser Gln Leu Gly Asp Phe Ile Glu Asp Ser Glu Ala Val Val
                405                 410                 415

Ala Val Asp Ala Val Ser Phe Thr Leu Leu Gln Asp Arg Leu Gln Asp
            420                 425                 430

Val Leu Glu Thr Leu Ser Glu Arg Glu Ala Gly Val Val Lys Leu Arg
        435                 440                 445

Phe Gly Leu Thr Asp Gly Met Pro Arg Thr Leu Asp Glu Ile Gly Gln
    450                 455                 460

Val Tyr Gly Val Thr Arg Glu Arg Ile Arg Gln Ile Glu Ser Lys Thr
465                 470                 475                 480

Met Ser Lys Leu Arg His Pro Ser Arg Ser Gln Val Leu Arg Asp Tyr
                485                 490                 495

Leu Asp
```

<210> SEQ ID NO 20
<211> LENGTH: 498
<212> TYPE: PRT
<213> ORGANISM: Artificial Sequence
<220> FEATURE:
<223> OTHER INFORMATION: SigA variant

<400> SEQUENCE: 20

```
Met Glu Ser Ser Met Val Glu Asn Val Ala Lys Thr Val Ala
1               5                   10                  15

Lys Lys Thr Ala Arg Lys Thr Ala Arg Lys Ala Ala Pro Arg Val Ala
                20                  25                  30

Thr Pro Leu Gly Val Ala Ser Glu Ser Pro Ile Ser Ala Thr Pro Ala
            35                  40                  45

Arg Ser Ile Asp Gly Thr Ser Thr Pro Val Glu Ala Ala Asp Thr Ile
        50                  55                  60

Glu Thr Thr Ala Pro Ala Ala Lys Ala Pro Ala Ala Lys Ala Pro Ala
65                  70                  75                  80

Lys Lys Val Ala Lys Lys Thr Ala Arg Lys Ala Pro Ala Lys Lys Thr
                85                  90                  95

Val Ala Lys Lys Ala Thr Thr Ala Lys Ala Ala Pro Ala Thr Ala Lys
            100                 105                 110

Asp Glu Asn Ala Pro Val Asp Asp Glu Glu Asn Leu Ala Gln Asp
        115                 120                 125

Glu Gln Asp Phe Asp Gly Asp Asp Phe Val Asp Gly Ile Glu Asp Glu
        130                 135                 140

Glu Asp Glu Asp Gly Val Glu Ala Leu Gly Glu Ser Glu Asp Asp
145                 150                 155                 160

Glu Glu Asp Gly Ser Ser Val Trp Asp Glu Asp Ser Ala Thr Leu
                165                 170                 175

Arg Gln Ala Arg Lys Asp Ala Glu Leu Thr Ala Ser Ala Asp Ser Val
            180                 185                 190

Arg Ala Tyr Leu Lys Gln Ile Gly Lys Val Ala Leu Leu Asn Ala Glu
        195                 200                 205

Gln Glu Val Ser Leu Ala Lys Arg Ile Glu Ala Gly Leu Tyr Ala Thr
    210                 215                 220

His Arg Met Glu Glu Met Glu Glu Ala Phe Ala Ala Gly Asp Lys Asp
225                 230                 235                 240

Ala Lys Leu Thr Pro Ala Val Lys Arg Asp Leu Arg Ala Asn Ala Arg
                245                 250                 255

Asp Gly Arg Lys Ala Lys Asn His Leu Leu Glu Ala Asn Leu Arg Leu
            260                 265                 270

Val Val Ser Leu Ala Lys Arg Tyr Thr Gly Arg Gly Met Ala Phe Leu
        275                 280                 285

Asp Leu Ile Gln Glu Gly Asn Leu Gly Leu Ile Arg Ala Val Glu Lys
    290                 295                 300

Phe Asp Tyr Ser Lys Gly Tyr Lys Phe Ser Thr Tyr Ala Thr Trp Trp
305                 310                 315                 320

Ile Arg Gln Ala Ile Thr Arg Ala Met Ala Asp Gln Ala Arg Thr Ile
                325                 330                 335

Arg Ile Pro Val His Met Val Glu Val Ile Asn Lys Leu Gly Arg Ile
            340                 345                 350

Gln Arg Glu Leu Leu Gln Glu Leu Gly Arg Glu Pro Thr Pro Gln Glu
        355                 360                 365
```

-continued

```
Leu Ser Lys Glu Met Asp Ile Ser Glu Glu Lys Val Leu Glu Ile Gln
370                 375                 380

Gln Tyr Ala Arg Glu Pro Ile Ser Leu Asp Gln Thr Ile Gly Asp Glu
385                 390                 395                 400

Gly Asp Ser Gln Leu Gly Asp Phe Ile Glu Asp Ser Glu Ala Val Val
                405                 410                 415

Ala Val Asp Ala Val Ser Phe Thr Leu Leu Gln Asp Gln Leu Gln Asp
                420                 425                 430

Val Leu Glu Thr Leu Ser Glu Arg Glu Ala Gly Val Val Lys Leu Arg
                435                 440                 445

Phe Gly Leu Thr Asp Gly Met Pro Arg Thr Leu Asp Glu Ile Gly Gln
450                 455                 460

Val Tyr Gly Val Thr Arg Glu Arg Ile Arg Gln Ile Glu Ser Lys Thr
465                 470                 475                 480

Met Ser Lys Leu Arg His Pro Ser Arg Ser Gln Val Leu Arg Asp Tyr
                485                 490                 495

Leu Asp
```

<210> SEQ ID NO 21
<211> LENGTH: 498
<212> TYPE: PRT
<213> ORGANISM: Artificial Sequence
<220> FEATURE:
<223> OTHER INFORMATION: SigA variant

<400> SEQUENCE: 21

```
Met Glu Ser Ser Met Val Glu Asn Asn Val Ala Lys Lys Thr Val Ala
1               5                   10                  15

Lys Lys Thr Ala Arg Lys Thr Ala Arg Lys Ala Ala Pro Arg Val Ala
                20                  25                  30

Thr Pro Leu Gly Val Ala Ser Glu Ser Pro Ile Ser Ala Thr Pro Ala
                35                  40                  45

Arg Ser Ile Asp Gly Thr Ser Thr Pro Val Glu Ala Ala Asp Thr Ile
50                  55                  60

Glu Thr Thr Ala Pro Ala Ala Lys Ala Pro Ala Ala Lys Ala Pro Ala
65                  70                  75                  80

Lys Lys Val Ala Lys Lys Thr Ala Arg Lys Ala Pro Ala Lys Lys Thr
                85                  90                  95

Val Ala Lys Lys Ala Thr Thr Ala Lys Ala Ala Pro Ala Thr Ala Lys
                100                 105                 110

Asp Glu Asn Ala Pro Val Asp Asp Glu Glu Asn Leu Ala Gln Asp
                115                 120                 125

Glu Gln Asp Phe Asp Gly Asp Phe Val Asp Gly Ile Glu Asp Glu
                130                 135                 140

Glu Asp Glu Asp Gly Val Glu Ala Leu Gly Glu Glu Ser Glu Asp Asp
145                 150                 155                 160

Glu Glu Asp Gly Ser Ser Val Trp Asp Glu Asp Glu Ser Ala Thr Leu
                165                 170                 175

Arg Gln Ala Arg Lys Asp Ala Glu Leu Thr Ala Ser Ala Asp Ser Val
                180                 185                 190

Arg Ala Tyr Leu Lys Gln Ile Gly Lys Val Ala Leu Leu Asn Ala Glu
                195                 200                 205

Gln Glu Val Ser Leu Ala Lys Arg Ile Glu Ala Gly Leu Tyr Ala Thr
                210                 215                 220
```

His Arg Met Glu Glu Met Glu Glu Ala Phe Ala Ala Gly Asp Lys Asp
225                 230                 235                 240

Ala Lys Leu Thr Pro Ala Val Lys Arg Asp Leu Arg Ala Ile Ala Arg
            245                 250                 255

Asp Gly Arg Lys Ala Lys Asn His Leu Leu Glu Ala Asn Leu Arg Leu
        260                 265                 270

Val Val Ser Leu Ala Lys Arg Tyr Thr Gly Arg Gly Met Ala Phe Leu
    275                 280                 285

Asp Leu Ile Gln Glu Gly Asn Leu Gly Leu Ile Arg Ala Val Glu Lys
290                 295                 300

Phe Asp Tyr Ser Lys Gly Tyr Lys Phe Ser Thr Tyr Ala Thr Trp Trp
305                 310                 315                 320

Ile Arg Gln Ala Ile Thr Arg Ala Met Ala Asp Gln Ala Arg Thr Ile
            325                 330                 335

Arg Ile Pro Val His Met Val Glu Val Ile Asn Lys Leu Gly Arg Ile
        340                 345                 350

Gln Arg Glu Leu Leu Gln Glu Leu Gly Arg Glu Pro Thr Pro Gln Glu
    355                 360                 365

Leu Ser Lys Glu Met Asp Ile Ser Glu Glu Lys Val Leu Glu Ile Gln
370                 375                 380

Gln Tyr Ala Arg Glu Pro Ile Ser Leu Asp Gln Thr Ile Gly Asp Glu
385                 390                 395                 400

Gly Asp Ser Gln Leu Gly Asp Phe Ile Glu Ser Glu Ala Val Val
            405                 410                 415

Ala Val Asp Ala Val Ser Phe Thr Leu Leu Gln Asp Gln Leu Gln Asp
        420                 425                 430

Val Leu Glu Thr Leu Ser Glu Arg Glu Ala Gly Val Val Lys Leu Arg
    435                 440                 445

Phe Gly Leu Thr Asp Gly Met Pro Arg Thr Leu Asp Glu Ile Gly Gln
450                 455                 460

Val Tyr Gly Val Thr Arg Glu Arg Ile Arg Gln Ile Glu Ser Lys Thr
465                 470                 475                 480

Met Ser Arg Leu Arg His Pro Ser Arg Ser Gln Val Leu Arg Asp Tyr
            485                 490                 495

Leu Asp

<210> SEQ ID NO 22
<211> LENGTH: 498
<212> TYPE: PRT
<213> ORGANISM: Artificial Sequence
<220> FEATURE:
<223> OTHER INFORMATION: SigA variant

<400> SEQUENCE: 22

Met Glu Ser Ser Met Val Glu Asn Asn Val Ala Lys Lys Thr Val Ala
1               5                   10                  15

Lys Lys Thr Ala Arg Lys Thr Ala Arg Lys Ala Ala Pro Arg Val Ala
            20                  25                  30

Thr Pro Leu Gly Val Ala Ser Glu Ser Pro Ile Ser Ala Thr Pro Ala
        35                  40                  45

Arg Ser Ile Asp Gly Thr Ser Thr Pro Val Glu Ala Ala Asp Thr Ile
    50                  55                  60

Glu Thr Thr Ala Pro Ala Ala Lys Ala Pro Ala Ala Lys Ala Pro Ala
65                  70                  75                  80

-continued

```
Lys Lys Val Ala Lys Thr Ala Arg Lys Ala Pro Ala Lys Lys Thr
             85                  90                  95

Val Ala Lys Lys Ala Thr Thr Ala Lys Ala Ala Pro Ala Thr Ala Lys
            100                 105                 110

Asp Glu Asn Ala Pro Val Asp Asp Glu Glu Asn Leu Ala Gln Asp
            115                 120                 125

Glu Gln Asp Phe Asp Gly Asp Asp Phe Val Asp Gly Ile Glu Asp Glu
            130                 135                 140

Glu Asp Glu Asp Gly Val Glu Ala Leu Gly Glu Glu Ser Glu Asp Asp
145                 150                 155                 160

Glu Glu Asp Gly Ser Ser Val Trp Asp Glu Asp Glu Ser Ala Thr Leu
            165                 170                 175

Arg Gln Ala Arg Lys Asp Ala Glu Leu Thr Ala Ser Ala Asp Ser Val
            180                 185                 190

Arg Ala Tyr Leu Lys Gln Ile Gly Lys Val Ala Leu Leu Asn Ala Glu
            195                 200                 205

Gln Glu Val Ser Leu Ala Lys Arg Ile Glu Ala Gly Leu Tyr Ala Thr
            210                 215                 220

His Arg Met Glu Glu Met Glu Glu Ala Phe Ala Ala Gly Asp Lys Asp
225                 230                 235                 240

Ala Lys Leu Thr Pro Ala Val Lys Arg Asp Leu Arg Ala Ile Ala Arg
            245                 250                 255

Asp Gly Arg Lys Ala Lys Asn His Leu Leu Glu Ala Asn Leu Arg Leu
            260                 265                 270

Val Val Ser Leu Ala Lys Arg Tyr Thr Gly Arg Gly Met Ala Phe Leu
            275                 280                 285

Asp Leu Ile Gln Glu Gly Asn Leu Gly Leu Ile Arg Ala Val Glu Lys
            290                 295                 300

Phe Asp Tyr Ser Lys Gly Tyr Lys Phe Ser Thr Tyr Ala Thr Trp Trp
305                 310                 315                 320

Ile Arg Gln Ala Ile Thr Arg Ala Met Ala Asp Gln Ala Arg Thr Ile
            325                 330                 335

Arg Ile Pro Val His Met Val Glu Val Ile Asn Lys Leu Gly Arg Ile
            340                 345                 350

Gln Arg Glu Leu Leu Gln Glu Leu Gly Arg Glu Pro Thr Pro Gln Glu
            355                 360                 365

Leu Ser Lys Glu Met Asp Ile Ser Glu Glu Lys Val Leu Glu Ile Gln
            370                 375                 380

Gln Tyr Ala Arg Glu Pro Ile Ser Leu Asp Gln Thr Ile Gly Asp Glu
385                 390                 395                 400

Gly Asp Ser Gln Leu Gly Asp Phe Ile Glu Asp Ser Glu Ala Val Val
            405                 410                 415

Ala Val Asp Ala Val Ser Phe Thr Leu Leu Gln Asp Gln Leu Gln Asp
            420                 425                 430

Val Leu Glu Thr Leu Ser Glu Arg Glu Ala Gly Val Val Lys Leu Arg
            435                 440                 445

Phe Gly Leu Thr Asp Gly Met Pro Arg Thr Leu Asp Glu Ile Gly Gln
            450                 455                 460

Val Tyr Gly Val Thr Arg Glu Arg Ile Arg Gln Ile Glu Ser Arg Thr
465                 470                 475                 480
```

```
Met Ser Lys Leu Arg His Pro Ser Arg Ser Gln Val Leu Arg Asp Tyr
                485                 490                 495

Leu Asp
```